US012692540B2

(12) United States Patent
You et al.

(10) Patent No.: US 12,692,540 B2
(45) Date of Patent: Jul. 28, 2026

(54) COMPOSITIONS AND METHODS FOR IMPROVING SEQUENCING SIGNALS

(71) Applicant: Illumina, Inc., San Diego, CA (US)

(72) Inventors: Huihong You, San Diego, CA (US); Samuel Caber, San Diego, CA (US); Michael Chesney, San Diego, CA (US); Jie Mao, San Diego, CA (US); Alexandre Richez, Cambridge (GB); Rebecca Macleod, San Diego, CA (US); Emily Welch, San Diego, CA (US); Zhong Mei, San Diego, CA (US); Xiaolin Wu, Cambridge (GB); Carole Anastasi, Cambridge (GB); Alexander Fuhrmann, Cambridge (GB)

(73) Assignee: Illumina, Inc., San Diego, CA (US)

( * ) Notice: Subject to any disclaimer, the term of this patent is extended or adjusted under 35 U.S.C. 154(b) by 582 days.

(21) Appl. No.: 18/192,288

(22) Filed: Mar. 29, 2023

(65) Prior Publication Data

US 2023/0357845 A1 Nov. 9, 2023

Related U.S. Application Data

(60) Provisional application No. 63/362,322, filed on Mar. 31, 2022.

(51) Int. Cl.

| | |
|---|---|
| ***C12Q 1/68*** | (2018.01) |
| ***C12N 9/12*** | (2006.01) |
| ***C12Q 1/6806*** | (2018.01) |
| ***C12Q 1/6874*** | (2018.01) |

(52) U.S. Cl.

CPC ......... *C12Q 1/6874* (2013.01); *C12N 9/1252* (2013.01); *C12Q 1/6806* (2013.01); *C12Y 207/07007* (2013.01)

(58) Field of Classification Search

CPC .................................................... C12Q 1/6869

See application file for complete search history.

(56) References Cited

U.S. PATENT DOCUMENTS

| | | | | |
|---|---|---|---|---|
| 5,302,509 | A | 4/1994 | Cheeseman | |
| 6,172,218 | B1 | 1/2001 | Brenner | |
| 6,465,178 | B2 | 10/2002 | Chappa et al. | |
| 2002/0110918 | A1* | 8/2002 | Davis | G01N 21/64 436/55 |
| 2010/0181535 | A1 | 7/2010 | Tinnefeld et al. | |
| 2014/0079923 | A1 | 3/2014 | George et al. | |
| 2015/0011731 | A1 | 1/2015 | Blanchard et al. | |
| 2018/0094140 | A1 | 4/2018 | Romanov | |
| 2018/0201981 | A1 | 7/2018 | Romanov | |
| 2018/0282791 | A1 | 10/2018 | Francais et al. | |
| 2019/0049380 | A1* | 2/2019 | Löbbert | G01N 21/77 |
| 2020/0131484 | A1 | 4/2020 | Golynskiy et al. | |
| 2020/0181587 | A1 | 6/2020 | Klausing et al. | |
| 2020/0277529 | A1 | 9/2020 | Romanov et al. | |
| 2020/0277670 | A1 | 9/2020 | Romanov et al. | |
| 2021/0155983 | A1 | 5/2021 | Wu et al. | |
| 2021/0188832 | A1 | 6/2021 | Romanov et al. | |
| 2022/0195517 | A1 | 6/2022 | Cressina et al. | |
| 2022/0380389 | A1 | 12/2022 | Callingham et al. | |
| 2023/0033699 | A1* | 2/2023 | Drmanac | C12Q 1/6874 |
| 2023/0313292 | A1 | 10/2023 | Callingham et al. | |
| 2024/0140939 | A1* | 5/2024 | Wu | C07H 19/10 |
| 2024/0141427 | A1 | 5/2024 | Golynskiy et al. | |

FOREIGN PATENT DOCUMENTS

| | | |
|---|---|---|
| WO | WO 98/44151 | 10/1998 |
| WO | WO 00/06770 | 2/2000 |
| WO | WO 00/18957 | 4/2000 |
| WO | WO 00/31148 | 6/2000 |
| WO | WO 01/01143 | 1/2001 |
| WO | WO 02/012566 | 2/2002 |
| WO | WO 03/014392 | 2/2003 |
| WO | WO 04/018493 | 3/2004 |
| WO | WO 04/018497 | 3/2004 |
| WO | WO 05/024010 | 3/2005 |
| WO | WO 05/047301 | 5/2005 |
| WO | WO 05/065814 | 7/2005 |
| WO | WO 06/120433 | 11/2006 |
| WO | WO 07/020457 | 2/2007 |
| WO | WO 13/041117 | 3/2013 |
| WO | WO 14/135221 | 9/2014 |
| WO | WO 14/139596 | 9/2014 |
| WO | WO 16/189287 | 12/2016 |
| WO | WO 17/051201 | 3/2017 |
| WO | WO 18/060482 | 4/2018 |
| WO | WO 18/129214 | 7/2018 |

(Continued)

OTHER PUBLICATIONS

International search report and written opinion dated Jul. 12, 2023 in International Application No. PCT/EP2023/058142.

Agrawal et al., May 2018, Measuring the refractive index, density, viscosity, pH, and surface tension of potassium thiocyanate (KSCN) solutions for refractive index matching in flow experiments, Journal of Chemical & Engineering Data, DOI:10.1021/acs/jced.7b00904, 11 pp.

Borrero-Echeverry et al., Jun. 24, 2016, Aqueous ammonium thiocyanate solutions as refractive index-matching fluids with low density and viscosity, arXiv:1605.p7562vw [physics.flu-dyn], 5 pp.

Margulies, Sep. 15, 2005, Genome sequencing in microfabricated high-density picolitre reactors, Nature, 437:376-380.

(Continued)

*Primary Examiner* — Kenneth R Horlick

(74) *Attorney, Agent, or Firm* — KNOBBE, MARTENS, OLSON & BEAR, LLP

(57) ABSTRACT

Embodiments of the present disclosure relate to compositions and kits for use in sequencing by synthesis to improve fluorescent signal intensity and reduce signal decay caused by short wavelength light source during the imaging events. Methods of sequencing using the compositions and kits described herein are also provided.

22 Claims, 1 Drawing Sheet

(56) References Cited

FOREIGN PATENT DOCUMENTS

| | | |
|---|---|---|
| WO | WO 20/097607 | 5/2020 |
| WO | WO 20/126593 | 6/2020 |
| WO | WO 00/53812 | 9/2020 |
| WO | WO 2021/213321 | 10/2021 |

OTHER PUBLICATIONS

Scheit, K. H. (1980). *Nucleotide analogs: Synthesis and biological function*. New York: John Wiley & Sons, TOC, 5 pages.
Schendure et al., Sep. 9, 2005, Accurate multiplex polony sequencing of an evolved bacterial genome, Science, 309(5741):1728-1732.
Uhlman et al., Jun. 1990, Antisense oligonucleotides: a new therapeutic principle, Chemical Reviews, 90(4):543-584.

* cited by examiner

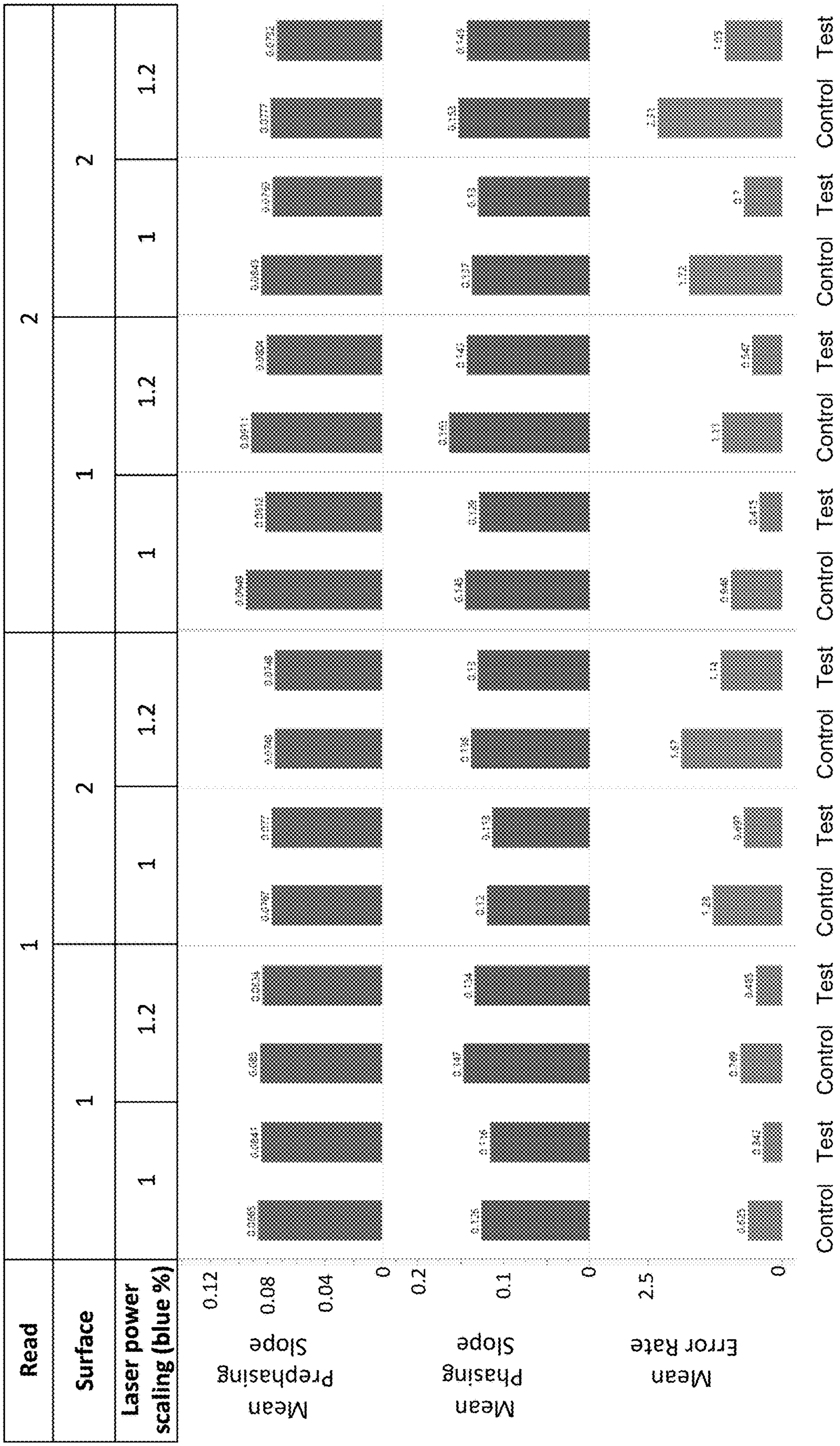
Read
Surface
Laser power scaling (blue %)
Mean Prephasing Slope
Mean Phasing Slope
Mean Error Rate
Control
Test

COMPOSITIONS AND METHODS FOR IMPROVING SEQUENCING SIGNALS

CROSS-REFERENCE TO RELATED APPLICATIONS

The present application claims the benefit of priority to U.S. Provisional Application No. 63/362,322, filed Mar. 31, 2022, the content of which is incorporated by reference in its entirety.

BACKGROUND

Field

The present disclosure relates to compositions and kits for use in nucleic acid sequencing for improving fluorescent signals.

Background

Non-radioactive detection of nucleic acids utilizing fluorescent labels is an important technology in molecular biology. Many procedures employed in recombinant DNA technology previously relied on the use of nucleotides or polynucleotides radioactively labeled with, for example $^{32}P$. Radioactive compounds permit sensitive detection of nucleic acids and other molecules of interest. However, there are serious limitations in the use of radioactive isotopes such as their expense, limited shelf life and more importantly safety considerations Eliminating the need for radioactive labels enhances safety whilst reducing the environmental impact and costs associated with, for example, reagent disposal. Methods amenable to non-radioactive fluorescent detection include by way of non-limiting example, automated DNA sequencing, hybridization methods, real-time detection of polymerase-chain-reaction products and immunoassays.

For many applications it is desirable to employ multiple spectrally distinguishable fluorescent labels in order to achieve independent detection of a plurality of spatially overlapping analytes. In such multiplex methods the number of reaction vessels may be reduced to simplify experimental protocols and facilitate the production of application-specific reagent kits. In multi-color automated DNA sequencing systems for example, multiplex fluorescent detection allows for the analysis of multiple nucleotide bases in a single electrophoresis lane, thereby increasing throughput over single-color methods, and reducing uncertainties associated with inter-lane electrophoretic mobility variations.

However, multiplex fluorescent detection can be problematic and there are a number of important factors that may constrain selection of appropriate fluorescent labels. First, it may be difficult to find dye compounds with suitably resolved absorption and emission spectra in a given application. In addition, when several fluorescent dyes are used together, generating fluorescence signals in distinguishable spectral regions by simultaneous excitation may be complicated because absorption bands of the dyes are usually widely separated, so it may be difficult to achieve comparable fluorescence excitation efficiencies even for two dyes. Another consideration of particular importance to molecular biology methods is the extent to which the fluorescent dyes must be compatible with reagent chemistries such as, for example, DNA synthesis solvents and reagents, buffers, polymerase enzymes, and ligase enzymes. Further, since many excitation methods use high power light sources like lasers, the fluorescent dyes must be sufficiently photo-stable to withstand multiple excitations.

For high-accuracy fluorescence identification of nucleobases, scanning of fluorescently labeled nucleotides under intensive expose to light is typically involved. Extensive laser irradiation, however, may bleach fluorescent dyes and/or damage nucleotide samples in solution/on flow-cell surface or those to which the fluorescent dyes are conjugated. Such expose to light may also cause DNA sample damage. Thus, there is a need particularly in multiplex fluorescent DNA sequencing to protect fluorescent dyes from photo-bleaching and polynucleotides from photo induced damages. The type and extent of photo-bleaching and photo-damages may vary depending on, for example, compound chemical structures and some their physical-chemical properties like redox potential, excitation spectra of particular bio-label, intensity of particular light source irradiation, and time of exposure in particular measurement. Since lower wavelength light sources are delivering higher energy photons, blue LED/laser having short (400-500 nm) wavelength emission (e.g., 450-460 nm) are more likely to cause photo-bleaching of dyes and associated with light DNA damage.

Performing fluorescent detection steps in an array context, such as sequencing by synthesis, can cause fluorescence signal intensity loss. The possible mechanisms that underlie this signal loss are numerous and can include cleavage of individual nucleic acid units from the solid support. There are also a number of chemical pathways by which nucleic acid damage can occur during irradiation in fluorescence detection. For example, it has been indicated that exposure to ultraviolet (UV) radiation can cause DNA damage via the direct photochemical [2+2] photocycloaddition reaction of thymine or cytosine to provide cyclobutane containing fused pyrimidine dimers, such as TT, TC, and CC. Such direct photocycloaddition reactions can occur in the UV B and UV C regions which extend from about 100 nm to about 315 nm. In the UV A region through a portion of the visible region, spanning from about 315 nm to about 500 nm, a complex mixture of indirect mechanisms can also cause DNA damage through photosensitization of other components. Such indirect mechanisms can result oxidative DNA modification via interaction with different light induced reactive species, for example, Reactive Oxygen Species (ROS) such as singlet oxygen, superoxide anion, and hydroxyl radical. Finally, it also has also known that quite a few ROS are generated by interaction of dye molecules in an excited state with oxygen molecules. Any combination of direct or indirect nucleic acid damage due to various reactions observed can be the underlying cause of fluorescence signal intensity loss observed in the array context.

Antioxidants, radical scavengers, triplet eliminators and different other compounds like Triplet State Quenchers (TSQ) have attracted attention due to their potential to mitigate photo-bleaching of fluorophores under high irradiance even in the presence of oxygen (See, for example, U.S. Publication No. 2010/0181535A1). Most intensively such additives and their conjugates were explored for "Green" and "Red" cyanine dyes (See, for example, U.S. Publication No. 2015/0011731A1). However, there still exists a need for developing compositions and kits to mitigate damage caused by shorter excitation wavelengths (e.g., 400~500 nm), where the light induced photobleaching and DNA damage are the most pronounced. For example, the signal decay of "blue dyes" caused by a blue light having a wavelength between 450 nm to 460 nm. In addition, there is a need to further reduce fluorescent signal intensity loss in sequencing by synthesis to facilitate sequencing of long nucleotide sequences, including sequences of 50, 75, 100, 200, and 500 nucleotides or more. Described herein in are compositions and kits for reducing fluorescent signal decay and improving signal intensity in nucleic acid sequencing.

SUMMARY

One aspect of the present disclosure relates to a method for reducing light-induced sequencing signal decay during sequencing by synthesis, comprising:

(i) contacting a solid support with an incorporation mixture comprising DNA polymerase and one more of four different types of nucleotides, wherein the solid support comprises a plurality of different target polynucleotides immobilized thereon, and sequencing primers that are complementary and hybridized to at least a portion of the target polynucleotides;

(ii) incorporating one type of nucleotides into the sequencing primers to produce extended copy polynucleotides, wherein one or more four types of nucleotides comprises a detectable label, and each of the four types of nucleotides comprises a 3' blocking group;

(iii) imaging and performing one or more fluorescent measurements of the extended copy polynucleotides in an aqueous scan mixture to determine the identity of the incorporated nucleotides; and (iv) removing the 3' blocking groups and the detectable labels of the incorporated nucleotides;

wherein the aqueous scan mixture comprises one or more additives for reducing fluorescent signal decay caused by the fluorescent measurements, and wherein the one or more additives comprise a salt or an ester of gallic acid, and one or more compounds selected from the group consisting of a triplet state quencher (TSQ), a radical scavenger (such as such as reactive oxygen species (ROS)), an oxygen scavenger, a reducing reagent, and combinations thereof.

One aspect of the present disclosure relates to a method for increasing sequencing signal intensity during sequencing by synthesis, comprising:

(i) contacting a solid support with an incorporation mixture comprising DNA polymerase and one more of four different types of nucleotides, wherein the solid support comprises a plurality of different target polynucleotides immobilized thereon, and sequencing primers that are complementary and hybridized to at least a portion of the target polynucleotides;

(ii) incorporating one type of nucleotides into the sequencing primers to produce extended copy polynucleotides, wherein one or more four types of nucleotides comprises a detectable label, and each of the four types of nucleotides comprises a 3' blocking group;

(iii) imaging and performing one or more fluorescent measurements of the extended copy polynucleotides in an aqueous scan mixture to determine the identity of the incorporated nucleotides; and (iv) removing the 3' blocking groups and the detectable labels of the incorporated nucleotides;

wherein the aqueous scan mixture comprises one or more antioxidants, and one or more high refractive index (RI) additives with no autofluorescence, and wherein the refractive index of the aqueous scan mixture is greater than about 1.35 at room temperature.

One aspect of the present disclosure relates to a kit for use with a sequencing apparatus, comprising a scan mixture composition, the scan mixture composition comprising: a salt or an ester of gallic acid; and one or more compounds selected from the group consisting of a triplet state quencher, a radical scavenger (e.g., a ROS), an oxygen scavenger, a reducing reagent, and combinations thereof.

Another aspect of the present disclosure relates to a kit for use with a sequencing apparatus, comprising a scan mixture composition, the scan mixture composition comprising: one or more antioxidants; and one or more high refractive index additives with no autofluorescence, wherein the refractive index of the aqueous scan mixture is greater than about 1.35 at room temperature, and wherein the one or more additives comprise an ionic liquid, a sugar, a carbohydrate, a polyol, polyether, an organic salt, an inorganic salt, an antioxidant, an amino acid, or combinations thereof.

BRIEF DESCRIPTION OF THE DRAWINGS

FIG. 1 illustrates the primary sequencing metrics of NovaSeg™ green/blue two channel sequencing by synthesis (SBS) using a standard scan mix as compared to an improved scan mix formulation according to an embodiment of the present disclosure.

DETAILED DESCRIPTION

Described herein are compositions and kits with additives for use during the imaging step of the sequencing by synthesis, and the methods of sequencing using the compositions and kits. Particularly, such compositions and kits can protect or mitigate against light induced fluorescent signal lost initiated or related DNA and/or nucleotides photo-damages and photo-bleaching of the fluorescent labeling compounds. Furthermore, such compositions and kits may also improve the fluorescent signal intensity and improves the overall sequencing data quality and facilitate longer read length.

As described in detail below, the new scan mixture compositions described herein may protect against fluorescent signal decay and improve signal intensity when exposed to a light source irradiation, in particular to the blue light with wavelength between about 400 nm to about 500 nm (e.g., about 450 nm to about 460 nm). These compositions also reduce DNA damages during sequencing runs.

Definition

The section headings used herein are for organizational purposes only and are not to be construed as limiting the subject matter described.

Unless defined otherwise, all technical and scientific terms used herein have the same meaning as is commonly understood by one of ordinary skill in the art. The use of the term "including" as well as other forms, such as "include", "includes," and "included," is not limiting. The use of the term "having" as well as other forms, such as "have", "has," and "had," is not limiting. As used in this specification, whether in a transitional phrase or in the body of the claim, the terms "comprise(s)" and "comprising" are to be interpreted as having an open-ended meaning. That is, the above terms are to be interpreted synonymously with the phrases "having at least" or "including at least." For example, when used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

As used herein, the term "covalently attached" or "covalently bonded" refers to the forming of a chemical bonding that is characterized by the sharing of pairs of electrons between atoms. For example, a covalently attached polymer coating refers to a polymer coating that forms chemical bonds with a functionalized surface of a substrate, as compared to attachment to the surface via other means, for example, adhesion or electrostatic interaction. It will be appreciated that polymers that are attached covalently to a surface can also be bonded via means in addition to covalent attachment.

As used herein, "cyclooctatetraene" (COT) is a compound with the structure

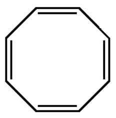

and the chemical formula $C_8H_8$, also known as 1,3,5,7-cyclooctatetraene, cycloocta-1,3,5,7 tetraene or [8]annulene. The dianion of COT (i.e., cyclooctatetraenide, $COT^{2-}$ or $[C_8H_8]^{2-}$) is aromatic. In some embodiments, COT may also refer to its positively- or negatively charged ion, (poly)ions, radical(s) or positively- or negatively charged ion-radical(s). It may also include optionally substituted analogs and derivatives thereof.

As used herein, a "nucleotide" includes a nitrogen containing heterocyclic base, a sugar, and one or more phosphate groups. They are monomeric units of a nucleic acid sequence. In RNA, the sugar is a ribose, and in DNA a deoxyribose, i.e., a sugar lacking a hydroxyl group that is present in ribose. The nitrogen containing heterocyclic base can be purine or pyrimidine base. Purine bases include adenine (A) and guanine (G), and modified derivatives or analogs thereof, such as deazapurine, 7-deazapurine such as 7-deaza adenine or 7-deaza guanine. Pyrimidine bases include cytosine (C), thymine (T), and uracil (U), and modified derivatives or analogs thereof. The C-1 atom of deoxyribose is bonded to N-1 of a pyrimidine or N-9 of a purine.

As used herein, a "nucleoside" is structurally similar to a nucleotide but is missing the phosphate moieties. An example of a nucleoside analogue would be one in which the label is linked to the base and there is no phosphate group attached to the sugar molecule. The term "nucleoside" is used herein in its ordinary sense as understood by those skilled in the art. Examples include, but are not limited to, a ribonucleoside comprising a ribose moiety and a deoxyribonucleoside comprising a deoxyribose moiety. A modified pentose moiety is a pentose moiety in which an oxygen atom has been replaced with a carbon and/or a carbon has been replaced with a sulfur or an oxygen atom. A "nucleoside" is a monomer that can have a substituted base and/or sugar moiety. Additionally, a nucleoside can be incorporated into larger DNA and/or RNA polymers and oligomers.

The term "purine base" is used herein in its ordinary sense as understood by those skilled in the art and includes its tautomers. Similarly, the term "pyrimidine base" is used herein in its ordinary sense as understood by those skilled in the art and includes its tautomers. A non-limiting list of optionally substituted purine-bases includes purine, deazapurine, 7-deazapurine, adenine, 7-deaza adenine, guanine, 7-deaza guanine, hypoxanthine, xanthine, alloxanthine, 7-alkylguanine (e.g., 7-methylguanine), theobromine, caffeine, uric acid and isoguanine. Examples of pyrimidine bases include, but are not limited to, cytosine, thymine, uracil, 5,6-dihydrouracil and 5-alkylcytosine (e.g., 5-methylcytosine).

As used herein, when an oligonucleotide or polynucleotide is described as "comprising" a nucleoside or nucleotide described herein, it means that the nucleoside or nucleotide described herein forms a covalent bond with the oligonucleotide or polynucleotide. Similarly, when a nucleoside or nucleotide is described as part of an oligonucleotide or polynucleotide, such as "incorporated into" an oligonucleotide or polynucleotide, it means that the nucleoside or nucleotide described herein forms a covalent bond with the oligonucleotide or polynucleotide. In some such embodiments, the covalent bond is formed between a 3' hydroxy group of the oligonucleotide or polynucleotide with the 5' phosphate group of a nucleotide described herein as a phosphodiester bond between the 3' carbon atom of the oligonucleotide or polynucleotide and the 5' carbon atom of the nucleotide.

As used herein, "derivative" or "analogue" means a synthetic nucleotide or nucleoside derivative having modified base moieties and/or modified sugar moieties. Such derivatives and analogs are discussed in, e.g., Scheit, *Nucleotide Analogs* (John Wiley & Son, 1980) and Uhlman et al., *Chemical Reviews* 90:543-584, 1990. Nucleotide analogs can also comprise modified phosphodiester linkages, including phosphorothioate, phosphorodithioate, alkyl-phosphonate, phosphoranilidate and phosphoramidate linkages. "Derivative", "analog" and "modified" as used herein, may be used interchangeably, and are encompassed by the terms "nucleotide" and "nucleoside" defined herein.

As used herein, the term "phosphate" is used in its ordinary sense as understood by those skilled in the art, and includes its protonated forms (for example,

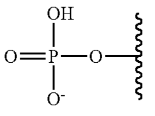 and 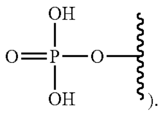).

As used herein, the terms "monophosphate," "diphosphate," and "triphosphate" are used in their ordinary sense as understood by those skilled in the art, and include protonated forms.

The terms "protecting group" and "protecting groups" as used herein refer to any atom or group of atoms that is added to a molecule in order to prevent existing groups in the molecule from undergoing unwanted chemical reactions. Sometimes, "protecting group" and "blocking group" can be used interchangeably.

As used herein, the prefixes "photo" or "photo-" mean relating to light or electromagnetic radiation. The term can encompass all or part of the electromagnetic spectrum including, but not limited to, one or more of the ranges commonly known as the radio, microwave, infrared, visible, ultraviolet, X-ray or gamma ray parts of the spectrum. The part of the spectrum can be one that is blocked by a metal region of a surface such as those metals set forth herein. Alternatively, or additionally, the part of the spectrum can be one that passes through an interstitial region of a surface such as a region made of glass, plastic, silica, or other material set forth herein. In particular embodiments, radiation can be used that is capable of passing through a metal.

Alternatively, or additionally, radiation can be used that is masked by glass, plastic, silica, or other material set forth herein.

As used herein, the term "phasing" refers to a phenomenon in SBS that is caused by incomplete removal of the 3' blocking groups and fluorescent labels, and failure to complete the incorporation of a portion of DNA strands within clusters by polymerases at a given sequencing cycle. Pre-phasing is caused by the incorporation of nucleotides without effective 3' blocking groups, wherein the incorporation event goes 1 cycle ahead due to a termination failure. Phasing and pre-phasing cause the measured signal intensities for a specific cycle to consist of the signal from the current cycle as well as noise from the preceding and following cycles. As the number of cycles increases, the fraction of sequences per cluster affected by phasing and pre-phasing increases, hampering the identification of the correct base. Pre-phasing can be caused by the presence of a trace amount of unblocked 3'-OH nucleotides during sequencing by synthesis (SBS). The unblocked 3'-OH nucleotides could be generated during the manufacturing processes or possibly during the storage and reagent handling processes.

As used herein the term "buffer," when used alone refers to a buffer solution not used as a detection solution. Buffer solutions include those used in polymerase reactions, hybridizations, washing, or any other operation performed prior to or after the use of the detection solution.

As used herein the term "phenolic compound" and "polyphenolic compound" refers to an aromatic compound having one- or multiple hydroxyl group(s) (i.e., phenolic groups) on a benzene or other aromatic- or heterocyclic ring. The benzene, or other aromatic/heterocyclic ring, can be optionally substituted with other substituents and/or fused rings. Exemplary polyphenolic compounds include, without limitation, trolox, gallic acid and lower alkyl esters thereof, monomethyl ethers thereof, and combinations of lower alkyl esters and monomethyl ethers thereof, pyrogallol, and hydroquinones, such as t-butyl hydroquinone (TBHQ), 2,4,5-trihydroxybutyrophenone (THBP).

As used herein, the term "high refractive index additive" refers to a compound when dissolved in water, provides a refractive index (RI) that is higher than the RI of water. In some embodiments, RI is measured at room temperature.

As used herein, the term "light-induced degradation" means the light-induced damage to one or more nucleic acids or polynucleotide strands in an array of nucleic acids by exposure to light illumination. Such degradation includes the complete or partial removal of individual nucleic acids from the support to which the array is attached. For example, light-induced degradation can include cleavage of the phosphodiester backbone at any of the nucleotides within an individual nucleic acid. Such degradation can also include removal of or reaction of a nucleic acid base or fluorescent tag causing a loss in hybridization or fluorescence function. Light-induced degradation can also include photo-induced crosslinking of nucleotides. The result of light-induced degradation can manifest as a decrease in fluorescence detection sensitivity in one or more regions or sub-arrays of an array nucleic acids when cycling through repeated detection steps, as might be observed, for example, when performing sequencing by synthesis, sequencing by ligation and microarray scanning. When used in conjunction with the term "inhibiting," this refers to a complete or partial block in the extent of damage, for example, as can be quantified by the observed strength of fluorescent emission. Light induced damage can be presented, for example, as a function of fluorescence signal intensity decay versus number of repeated irradiation (detection) steps performed on the array of nucleic acids. This process is sometimes referred to as "signal intensity decay" or "signal decay." Another assessment of light damage can be estimated as a function of sequencing error rate versus number of repeated irradiation (detection) steps performed on the array of nucleic acids.

Methods of Reducing Light-Induced Signal Decay

One aspect of the present disclosure relates to a method for reducing light-induced sequencing signal decay during sequencing by synthesis, comprising:

imaging and performing one or more fluorescent measurements of a plurality of extended copy polynucleotides in an aqueous scan mixture to determine the identity of incorporated nucleotides;

wherein the aqueous scan mixture comprises one or more additives for reducing fluorescent signal decay caused by the fluorescent measurements, and wherein the one or more additives comprise a salt or an ester of gallic acid, and one or more compounds selected from the group consisting of a triplet state quencher (TSQ), a radical scavenger (such as ROS), an oxygen scavenger, a reducing reagent, and combinations thereof. In some further embodiments, the aqueous scan mixture comprises the salt or the ester of gallic acid, and two, three, four or more compounds selected from the group consisting of a triplet state quencher (TSQ), a radical scavenger (such as ROS), an oxygen scavenger, a reducing reagent, and combinations thereof.

In particular, the method for reducing light-induced sequencing signal decay during sequencing by synthesis may comprise:

(i) contacting a solid support with an incorporation mixture comprising DNA polymerase and one more of four different types of nucleotides, wherein the solid support comprises a plurality of different target polynucleotides immobilized thereon, and sequencing primers that are complementary and hybridized to at least a portion of the target polynucleotides;

(ii) incorporating one type of nucleotides into the sequencing primers to produce extended copy polynucleotides, wherein one or more four types of nucleotides comprises a detectable label, and each of the four types of nucleotides comprises a 3' blocking group;

(iii) imaging and performing one or more fluorescent measurements of the extended copy polynucleotides in an aqueous scan mixture to determine the identity of the incorporated nucleotides; and (iv) removing the 3' blocking groups and the detectable labels of the incorporated nucleotides;

wherein the aqueous scan mixture comprises one or more additives for reducing fluorescent signal decay caused by the fluorescent measurements, and wherein the one or more additives comprise a salt or an ester of gallic acid, and one or more compounds selected from the group consisting of a triplet state quencher (TSQ), a radical scavenger (such as ROS), an oxygen scavenger, a reducing reagent, and combinations thereof.

In some embodiments of the method described herein, the aqueous scan mixture comprises the salt or ester of gallic acid, and at least one TSQ. In some other embodiments, the aqueous scan mixture comprises the salt or ester of gallic acid, and at least one radical scavenger. In some other embodiments, the aqueous scan mixture comprises the salt or ester of gallic acid, and at least one oxygen scavenger. In some other embodiments, the aqueous scan mixture comprises the salt or ester of gallic acid, and at least one reducing reagent. In some further embodiments, the aqueous scan mixture comprises the salt or ester of gallic acid, at least one TSQ and at least one radical scavenger. In some further embodiments, the aqueous scan mixture comprises the salt or ester of gallic acid, at least one TSQ, and at least one oxygen scavenger. In some further embodiments, the aqueous scan mixture comprises the salt or ester of gallic acid, at least one TSQ, and at least one reducing reagent. In some other embodiments, the aqueous scan mixture comprises the salt or ester of gallic acid, at least one radical scavenger, and at least one oxygen scavenger. In some other embodiments, the aqueous scan mixture comprises the salt or ester of gallic acid, at least one radical scavenger, and at least one reducing reagent. In some other embodiments, the aqueous scan mixture comprises the salt or ester of gallic acid, at least one oxygen scavenger, and at least one reducing reagent.

In some embodiments of the method described herein, the radical scavenger comprises or is a reactive oxygen species (ROS) scavenger. In further embodiments, the oxygen scavenger comprises or is an 02 scavenger. In some embodiments, the aqueous scan mixture comprises the salt or ester of gallic acid, and at least one TSQ. In further embodiments, the aqueous scan mixture further comprises at least one oxygen scavenger or at least one reducing reagent. In some further embodiments, the aqueous scan mixture comprises the salt or ester of gallic acid, at least one TSQ, at least one oxygen scavenger, and at least one reducing reagent. Non-limiting examples of TSQ include a nickel (II) salt or complex, cyclooctatetraene (COT) or a substituted analog thereof, 2-mercaptoethylamine (MEA) or a salt thereof, 6-hydroxy-2,5,7,8-tetramethylchroman-2-carboxylic acid (Trolox) or a salt thereof, or combinations thereof. Non-limiting examples of the oxygen scavenger include an enzyme capable of reacting with oxygen, glucose oxidase, catalase, diethylhydroxylamine (DEHA), or hydroquinone, or combinations thereof. Non-limiting examples of the radical scavenger include 1,4-diazabicyclo[2.2.2]octane (DABCO), caffeine, mannitol, or combinations thereof. Non-limiting examples of the reducing reagent include a phosphine or a salt thereof, sodium sulfite ($Na_2SO_3$), a thiol containing compound, 2-mercaptoethanol (bME), cysteine or an analog thereof, and combinations thereof. For example, the phosphine may comprise tris(hydroxypropyl) phosphine (THP), tris(hydroxymethyl)phosphine (THMP), tris(carboxyethyl)phosphine (TCEP), bis(p-sulfonatophenyl)phenylphosphine dihydrate potassium salt, or triphenylphosphine-3,3',3"-trisulfonic acid trisodium salt. In one embodiment, the aqueous scan mixture comprises 2-hydroxylethyl gallate (HEG), a salt of MEA (2-mercaptoethylamine HCl), Trolox, 2-mercaptoethanol, and cysteine or an analog thereof. In further embodiments, cysteine may include N-acetyl cysteine or L-cysteine, or a combination thereof. In another embodiment, the aqueous scan mixture comprises 2-hydroxylethyl gallate, an MEA salt (2-mercaptoethylamine HCl), Trolox, 2-mercaptoethanol, N-acetyl cysteine and/or L-cysteine. In some embodiments, the aqueous scan mix may further comprise an ascorbate salt (e.g., sodium ascorbate). In other embodiments, the aqueous scan mix does not comprise an ascorbate salt (e.g., sodium ascorbate). Without being bound by a particular theory, certain reaction in scan mixture containing sodium ascorbate and HEG showed loss of entire fluorophore (where ffN has an azide containing cleavable linker such as LN3), suggesting that sodium ascorbate may mediated blue laser induced azide degradation and nitrene formation. In some embodiments, the concentration of each of the additives for reducing the signal decay in the aqueous scan mixture may range from about 1 mM to about 200 mM, from about 2 mM to about 100 mM, from about 5 mM to about 50 mM, or from about 10 mM to about 25 mM. In further embodiments, the concentration may be about 1 mM, 2 mM, 5 mM, 10 mM, 15 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, or 100 mM, or a range defined by any two of the preceding values.

In some embodiments of the method described herein, the aqueous scan mixture may further comprise one or more buffering agents (e.g., Tris, glycine, MOPS, HEPES, etc.) or surfactants (e.g., Tween 20), or combinations thereof. In some embodiments, the aqueous scan mixture has a basic pH of from about 7.2 to about 8.0, for example, about 7.2, 7.3, 7.4, 7.5, 7.6, 7.7, 7.8, 7.9 or 8.0, or a range defined by any two of the preceding values.

In some embodiments of the method described herein, step (iii) comprising using two light sources operating at wavelengths between about 400 nm to about 550 nm (e.g., between 450-460 nm and between 520-535 nm). In other embodiments, step (iii) comprising using a single source operating at a wavelength between about 400 nm to about 550 nm (e.g., 450-460 nm).

In some embodiments of the method described herein, the method further comprises step (v) contacting the solid support with an aqueous wash solution. In further embodiments, wherein steps (i) through (v) are repeated at least about 50, 100, 150, 200, 250, 300, 350, 400, 450 or 500 cycles to determine the target polynucleotides sequences.

In any embodiments of the method described herein, the method reduces sequencing signal decay by at least 10%, 15%, 20%, 25%, 30%, 35%, 40%, 45% or 50% after about 50, 100, 150, 200, 250, 300, 350, 400, 450 or 500 cycles, when comparing to the method using an aqueous scan mixture without the one or more compounds selected from the group consisting of a TSQ, an oxygen scavenger, a reducing reagent, and combinations thereof. In further embodiments, the method reduces sequencing signal decay by at least 10%, 15%, 20%, 25%, 30%, 35%, 40%, 45% or 50% after about 50, 100, 150, 200, 250, 300, 350, 400, 450 or 500 cycles, when comparing to the same method using a standard aqueous scan mixture comprising an ascorbate salt and gallic acid (or a salt or ester thereof such as HEG). In a particular example, the standard scan mixture is also known as universal scan mix (USM) having the following components: Tris (1M), Tween 20 (0.05%), sodium ascorbate (20 mM), and HEG (10 mM). In further embodiments, the method reduces sequencing error rate, percent phasing value, or percent prephasing value by at least 10%, 15%, 20%, 25%, 30%, 35%, 40%, 45% or 50% after about 50, 100, 150, 200, 250, 300, 350, 400, 450 or 500 cycles, when comparing to the method using an aqueous scan mixture without the one or more compounds selected from the group consisting of a TSQ, a radical scavenger, an oxygen scavenger, a reducing reagent, and combinations thereof. In further embodiments, the method reduces sequencing error rate, percent phasing value, or percent prephasing value by at least 10%, 15%, 20%, 25%, 30%, 35%, 40%, 45% or 50% after about 50, 100, 150, 200, 250, 300, 350, 400, 450 or 500 cycles, when comparing to the same method using a standard aqueous scan mixture comprising an ascorbate salt and gallic acid (or a salt or ester thereof such as HEG), for example, the same method using USM.

Methods of Increasing Signal Intensity

Another aspect of the present disclosure relates to a method for increasing sequencing signal intensity during sequencing by synthesis, comprising:

imaging and performing one or more fluorescent measurements of a plurality of extended copy polynucleotides in an aqueous scan mixture to determine the identity of incorporated nucleotides;

wherein the aqueous scan mixture comprises one or more antioxidants, and one or more high refractive index (RI) additives with no autofluorescence, and wherein the refractive index of the aqueous scan mixture is greater than about 1.35 at room temperature.

In some embodiments, the method for increasing sequencing signal intensity during sequencing by synthesis may comprise:

(i) contacting a solid support with an incorporation mixture comprising DNA polymerase and one more of four different types of nucleotides, wherein the solid support comprises a plurality of different target polynucleotides immobilized thereon, and sequencing primers that are complementary and hybridized to at least a portion of the target polynucleotides;

(ii) incorporating one type of nucleotides into the sequencing primers to produce extended copy polynucleotides, wherein one or more four types of nucleotides comprises a detectable label, and each of the four types of nucleotides comprises a 3' blocking group;

(iii) imaging and performing one or more fluorescent measurements of the extended copy polynucleotides in an aqueous scan mixture to determine the identity of the incorporated nucleotides; and (iv) removing the 3' blocking groups and the detectable labels of the incorporated nucleotides;

wherein the aqueous scan mixture comprises one or more antioxidants, and one or more high refractive index (RI) additives with no autofluorescence, and wherein the refractive index of the aqueous scan mixture is greater than about 1.35 at room temperature.

In some embodiments of the method described herein, the refractive index of the aqueous scan mixture is about 1.36 to about 1.5, for example, about 1.36, 1.37, 1.38, 1.39, 1.40, 1.41, 1.42, 1.43, 1.44, 1.45, 1.45, 1.47, 1.48, 1.49 or 1.50, or a range defined by any two of the preceding values. In some further embodiments, the RI of the scan mix is similar to that of the solid support used for SBS (e.g., flowcell).

In some embodiments of the method described herein, wherein one or more additives comprise an ionic liquid, a sugar, a carbohydrate, a polyol, polyether, an organic salt, an inorganic salt, an antioxidant, an amino acid, or combinations thereof. Non-limiting examples of ionic liquid includes 1-benzyl-3-methylimidazolium chloride ([Bzmim]Cl) or sodium dodecyl sulfate (SDS), and combinations thereof. In some such embodiments, the aqueous scan mixture comprises ([Bzmim]Cl in a concentration from about 200 mg/mL to about 1000 mg/mL, or from about 300 mg/mL to about 500 mg/mL. In some embodiments, the aqueous scan mix may comprise one or more sugars (monosaccharide, disaccharide, or polysaccharide), such as sucrose, or glucose. In further embodiments, the aqueous scan mixture comprises a sugar (sucrose or glucose) in a concentration from about 250 mg/mL to about 500 mg/mL, from about 300 mg/mL to about 450 mg/mL, or about 400 mg/mL. In one embodiment, the additives in the aqueous scan mixture comprise glycine, sucrose, and KCl. In another embodiment, the additives in the aqueous scan mixture comprise glycine, glycerol, and NaCl. In still another embodiment, the additives in the aqueous scan mixture comprise glycine, glucose, and KCl. In still another embodiment, the additives in the aqueous scan mixture comprise threonine, sucrose and KCl. The concentration of the additives (e.g., sugars, amino acids, or inorganic salts) in the scan mixture may range from about 1 mg/mL to about 500 mg/mL, about 5 mg/mL to about 400 mg/mL, from about 10 mg/mL to about 300 mg/mL, from about 20 mg/mL to about 200 mg/mL, from about 40 mg/mL to about 100 mg/mL. In further embodiments, the concentration of the additives may be about 1 mg/mL, 5 mg/mL, 10 mg/mL, 20 mg/mL, 30 mg/mL, 40 mg/mL, 50 mg/mL, 60 mg/mL, 70 mg/mL, 80 mg/mL, 90 mg/mL, 100 mg/mL, 110 mg/mL, 120 mg/mL, 130 mg/mL, 140 mg/mL, 150 mg/mL, 160 mg/mL, 170 mg/mL, 180 mg/mL, 190 mg/mL or 200 mg/mL, or a range defined by any two of the preceding values. In further embodiments, the concentration of the additives (e.g., polyols) may be about 1%, 2%, 3%, 4%, 5%, 6%, 7%, 8%, 9%, 10%, 12%, 14%, 16%, 18% or 20% by weight of the total aqueous scan mix, or in a range defined by any two of preceding values.

In some embodiments of the method described herein, the viscosity of the aqueous scan mixture is less than about 5 cP, 4.5 cP, 4 cP, 3.5 cP, 3 cP, 2.5 cP, 2 cP, 1.5 cP or 1 cP. The viscosity limit of the aqueous scan mixture may depend on the sequencing platform used and/or the fluidics of the system. In some embodiments, the aqueous scan mixture may be less than about 3 cP to avoid putting too much pressure in the fluidic system. In some further embodiments, viscosity may be measured at room temperature (e.g., between 20 to 25° C.) using a RheoSense microVISC™ instrument.

In some embodiments of the method described herein, the aqueous scan mixture may further comprise one or more buffering agents (e.g., Tris, glycine, etc.) or surfactants (e.g., Tween 20), or combinations thereof. In some embodiments, the aqueous scan mixture has a basic pH of from about 7.2 to about 8.0, for example, about 7.2, 7.3, 7.4, 7.5, 7.6, 7.7, 7.8, 7.9 or 8.0, or a range defined by any two of the preceding values.

In some embodiments of the method described herein, step (iii) comprising using two light sources operating at wavelengths between about 400 nm to about 550 nm (e.g., between 450-460 nm and between 520-535 nm). In other embodiments, step (iii) comprising using a single source operating at a wavelength between about 400 nm to about 550 nm (e.g., 450-460 nm).

In some embodiments of the method described herein, the method further comprises step (v) contacting the solid support with an aqueous wash solution. In further embodiments, wherein steps (i) through (v) are repeated at least about 50, 100, 150, 200, 250, 300, 350, 400, 450 or 500 cycles to determine the target polynucleotides sequences.

In any embodiments of the method described herein, the method increases sequencing signal intensity or boosts the signals by at least 10%, 15%, 20%, 25%, 30%, 35%, 40%, 45% or 50% after about 50, 100, 150, 200, 250 or 300 cycles, when comparing to the method using an aqueous scan mixture, such as a standard scan mixture without the one or more high RI additives described herein. In a particular example, the standard scan mixture is also known as universal scan mix (USM) having the following components: Tris (1M) Tween 20 (0.05%), sodium ascorbate (20 mM), and HEG (10 mM). In further embodiments, the method reduces sequencing error rate, percent phasing value, or percent prephasing value by at least 10%, 15%, 20%, 25%, 30%, 35%, 40%, 45% or 50% after about 50, 100, 150, 200, 250, 300, 350, 400, 450 or 500 cycles, when comparing to the method using an aqueous scan mixture (such as USM or VSM) without the one or more high RI additives described herein.

In any embodiments of the method of increasing signal intensity as described herein, the aqueous scan mixture may further comprise one or more antioxidants such as sodium ascorbate, HEG, gallic acid, or combinations thereof. In addition, the scan mixture may further comprise any of the compounds selected from the group consisting of a triplet state quencher, an oxygen scavenger, a reducing reagent, and combinations thereof as described in the method in connection with reducing sequencing signal decay.

Kits

One aspect of the present disclosure relates to a kit for use with a sequencing apparatus for reducing sequencing signal decay, comprising a scan mixture composition, the scan mixture composition comprising: a salt or an ester of gallic acid; and one, two, three, four or more compounds selected from the group consisting of a triplet state quencher, a radical scavenger (e.g., ROS), an oxygen scavenger), a reducing reagent, and combinations thereof.

In some embodiments of the kit described herein, the aqueous scan mixture comprises the salt or ester of gallic acid, and one or more TSQs. In some other embodiments, the aqueous scan mixture comprises the salt or ester of gallic acid, and one or more radical scavengers. In some other embodiments, the aqueous scan mixture comprises the salt or ester of gallic acid, and one or more oxygen scavengers. In some other embodiments, the aqueous scan mixture comprises the salt or ester of gallic acid, and one or more reducing reagents. In some further embodiments, the aqueous scan mixture comprises the salt or ester of gallic acid, one or more TSQs, and one or more radical scavengers. In some further embodiments, the aqueous scan mixture comprises the salt or ester of gallic acid, one or more TSQs, and one or more oxygen scavengers. In some further embodiments, the aqueous scan mixture comprises the salt or ester of gallic acid, one or more TSQs, and one or more reducing reagents. In some other embodiments, the aqueous scan mixture comprises the salt or ester of gallic acid, one or more radical scavengers, and one or more oxygen scavengers. In some other embodiments, the aqueous scan mixture comprises the salt or ester of gallic acid, one or more radical scavengers, and one or more reducing reagents. In some other embodiments, the aqueous scan mixture comprises the salt or ester of gallic acid, one or more oxygen scavengers, and one or more reducing reagents.

In some embodiments of the kits described herein, the radical scavenger comprises or is an oxygen scavenger. In further embodiments, the oxygen scavenger comprises an $O_2$ scavenger. The radical scavenger may comprise a singlet oxygen scavenger, or a ROS scavenger, or a combination thereof. In some embodiments, the aqueous scan mixture comprises the salt or ester of gallic acid, and at least one TSQ. In further embodiments, the aqueous scan mixture further comprises at least one oxygen scavenger or at least one reducing reagent. In some further embodiments, the aqueous scan mixture comprises the salt or ester of gallic acid, at least one TSQ, at least one oxygen scavenger, and at least one reducing reagent. Non-limiting examples of TSQ include a nickel (II) salt or complex, COT or a substituted analog thereof, MEA or a salt thereof, Trolox or a salt thereof, and combinations thereof. Non-limiting examples of the oxygen scavenger include an enzyme capable of reacting with oxygen, glucose oxidase, catalase, DEHA, or hydroquinone or combinations thereof. Non-limiting examples of the radical scavenger include DABCO, caffeine, mannitol, or combinations thereof. Non-limiting examples of the reducing reagent include a phosphine or a salt thereof, $Na_2SO_3$, a thiol containing compound, bME, cysteine or an analog thereof, and combinations thereof. For example, the phosphine may comprise THP, THMP, TCEP, bis(p-sulfonatophenyl)phenylphosphine dihydrate potassium salt, or triphenylphosphine-3,3',3"-trisulfonic acid trisodium salt. In one embodiment, the aqueous scan mixture comprises HEG, a salt of MEA (e.g., 2-mercaptoethylamine HCl), Trolox, 2-mercaptoethanol, and cysteine or an analog thereof. In further embodiments, cysteine may include N-acetyl cysteine or L-cysteine, or a combination thereof. In another embodiment, the aqueous scan mixture comprises 2-hydroxylethyl gallate, a salt of MEA (e.g., 2-mercaptoethylamine HCl), Trolox, 2-mercaptoethanol, N-acetyl cysteine and/or L-cysteine. In some embodiments, the aqueous scan mix may further comprise an ascorbate salt (e.g., sodium ascorbate). In other embodiments, the aqueous scan mix does not comprise an ascorbate salt (e.g., sodium ascorbate). In some embodiments, the concentration of each of the additives for reducing the signal decay in the aqueous scan mixture may range from about 1 mM to about 200 mM, from about 2 mM to about 100 mM, from about 5 mM to about 50 mM, or from about 10 mM to about 25 mM. In further embodiments, the concentration may be about 1 mM, 2 mM, 5 mM, 10 mM, 15 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, or 100 mM, or a range defined by any two of the preceding values.

In some embodiments of the kit described herein, the aqueous scan mixture may further comprise one or more buffering agents (e.g., Tris, glycine, MOPS, HEPES, etc.) or surfactants (e.g., Tween 20), or combinations thereof. In some embodiments, the aqueous scan mixture has a basic pH of from about 7.2 to about 8.0, for example, about 7.2, 7.3, 7.4, 7.5, 7.6, 7.7, 7.8, 7.9 or 8.0, or a range defined by any two of the preceding values.

Another aspect of the present disclosure relates to a kit for use with a sequencing apparatus to for increasing the signal intensity, comprising a scan mixture composition, the scan mixture composition comprising: one or more antioxidants; and one or more high refractive index additives with no autofluorescence, wherein the refractive index of the aqueous scan mixture is greater than about 1.35 at room temperature, and wherein the one or more additives comprise an ionic liquid, a sugar, a carbohydrate, a polyol, polyether, an organic salt, an inorganic salt, an antioxidant, an amino acid, or combinations thereof. In some embodiments, the refractive index of the aqueous scan mixture is about 1.36 to about 1.5, for example, about 1.36, 1.37, 1.38, 1.39, 1.40, 1.41, 1.42, 1.43, 1.44, 1.45, 1.45, 1.47, 1.48, 1.49 or 1.50, or a range defined by any two of the preceding values.

In some embodiments of the kit described herein, wherein one or more additives comprise an ionic liquid, a sugar, a carbohydrate, a polyol, polyether, an organic salt, an inorganic salt, an antioxidant, an amino acid, or combinations thereof. Non-limiting examples of ionic liquid includes [Bzmim]Cl or sodium dodecyl sulfate, and combinations thereof. In some such embodiments, the aqueous scan mixture comprises [Bzmim]Cl in a concentration from about 200 mg/mL to about 1000 mg/mL, or from about 300 mg/mL to about 500 mg/mL. In some embodiments, the aqueous scan mix may comprise one or more sugars (monosaccharide, disaccharide, or polysaccharide), such as sucrose, or glucose. In further embodiments, the aqueous scan mixture comprises a sugar (sucrose or glucose) in a concentration from about 250 mg/mL to about 500 mg/mL, from about 300 mg/mL to about 450 mg/mL, or about 400 mg/mL. In one embodiment, the additives in the aqueous scan mixture comprise glycine, sucrose, and KCl. In another embodiment, the additives in the aqueous scan mixture comprise glycine, glycerol, and NaCl. In still another embodiment, the additives in the aqueous scan mixture comprise glycine, glucose, and KCl. In still another embodiment, the additives in the aqueous scan mixture comprise threonine, sucrose and KCl. The concentration of the additives (e.g., sugars, amino acids, or inorganic salts) in the scan mixture may range from about 1 mg/mL to about 500 mg/mL, about 5 mg/mL to about 400 mg/mL, from about 10 mg/mL to about 300 mg/mL, from about 20 mg/mL to about 200 mg/mL, from about 40 mg/mL to about 100 mg/mL. In further embodiments, the concentration of the additives may be about 1 mg/mL, 5 mg/mL, 10 mg/mL, 20 mg/mL, 30 mg/mL, 40 mg/mL, 50 mg/mL, 60 mg/mL, 70 mg/mL, 80 mg/mL, 90 mg/mL, 100 mg/mL, 110 mg/mL, 120 mg/mL, 130 mg/mL, 140 mg/mL, 150 mg/mL, 160 mg/mL, 170 mg/mL, 180 mg/mL, 190 mg/mL or 200 mg/mL, or a range defined by any two of the preceding values. In further embodiments, the concentration of the additives (e.g., polyols) may be about 1%, 2%, 3%, 4%, 5%, 6%, 7%, 8%, 9%, 10%, 12%, 14%, 16%, 18% or 20% by weight of the total aqueous scan mix, or in a range defined by any two of preceding values.

In further embodiments, the aqueous scan mixture may further comprise one or more antioxidants such as sodium ascorbate, HEG, gallic acid, or combinations thereof. In addition, the scan mixture may further comprise any of the compounds selected from the group consisting of a triplet state quencher, an oxygen scavenger, a reducing reagent, and combinations thereof as described in the kit for reducing sequencing signal decay.

In some embodiments of the kit described herein, the viscosity of the aqueous scan mixture is less than about 5 cP, 4.5 cP, 4 cP, 3.5 cP, 3 cP, 2.5 cP, 2 cP, 1.5 cP or 1 cP. The viscosity limit of the aqueous scan mixture may depend on the sequencing platform used and/or the fluidics of the system. In some embodiments, the aqueous scan mixture may be less than about 3 cP to avoid putting too much pressure in the fluidic system. In some further embodiments, viscosity may be measured at room temperature (e.g., between 20 to 25° C. such as 23° C.) using a RheoSense microVISC™ instrument.

In any embodiments of the kits described herein, the kit may further include an incorporation mixture composition for incorporating 3' blocked, labeled nucleotides into copy polynucleotide strands complementary to at least a portion of template polynucleotide strands, wherein the incorporation mixture composition comprises:

one or more different types of labeled nucleotides, wherein each of the labeled nucleotides comprises a 3' blocking group; and a DNA polymerase.

In any embodiments of the kits described herein, the kit may further include a cleavage mixture composition, wherein the cleavage mixture composition comprises a reagent for removing the label and the 3' blocking group of the incorporated nucleotides.

In any embodiments of the kits described herein, the kit may comprise a plurality of chambers, and each chamber contains a different composition.

In any embodiments of the kits described herein, the kit further comprises a DNA polymerase (such as a mutant of 9° N polymerase, such as those disclosed in WO 2005/024010, U.S. Publication Nos. 2020/0131484 A1, 2020/0181587 A1, and U.S. Ser. Nos. 63/412,241 and 63/433,971, each of which is incorporated by reference herein in its entirety) and one or more buffer compositions.

Alternatively, the kit may comprise one or more different types of unlabeled 3' blocked nucleotide and one or more affinity reagents (e.g., protein tags and antibodies) for use in a modified method of sequencing as described herein.

In any embodiments of the kits described herein, the kit may be used in a sequencing platform with two light sources operating at between about 400 nm to about 550 nm (e.g., between 450-460 nm and between 520-535 nm). In other embodiments, the kit may also be used in a sequencing platform with a single source operating at a wavelength between about 400 nm to about 550 nm (e.g., 450-460 nm).

Incorporation Mix Containing Labeled Nucleotides

An incorporation mix described herein may include one or more nucleotides labeled with a detectable label having the formula:

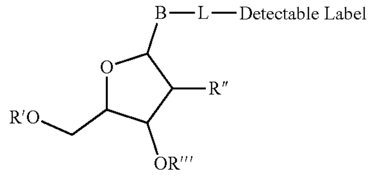

where a Detectable Label may include a fluorescent dye moiety; B is a nucleobase, such as, for example uracil, thymine, cytosine, adenine, 7-deaza adenine, guanine, 7-deaza guanine, and the like; L is an optional linker which may or may not be present; R' can be H, or —OR' is monophosphate, diphosphate, triphosphate, thiophosphate, a phosphate ester analog, —O— attached to a reactive phosphorous containing group, or —O— protected by a blocking group; R" is H or OH; and R"' is H, a 3' blocking group described herein, or —OR"' forms a phosphoramidite. Where —OR"' is phosphoramidite, R' is an acid-cleavable hydroxyl protecting group which allows subsequent monomer coupling under automated synthesis conditions. In some further embodiments, B comprises

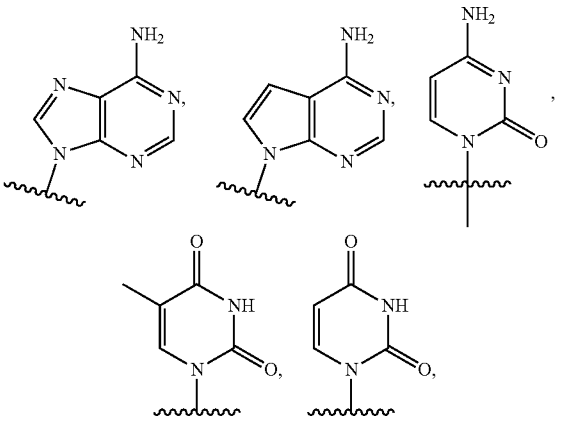

-continued

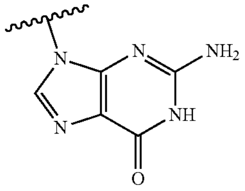

or

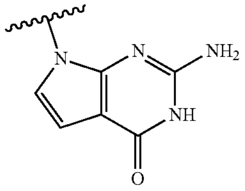

, or optionally substituted derivatives and analogs thereof. In some further embodiments, the labeled nucleobase comprises the structure

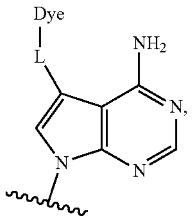

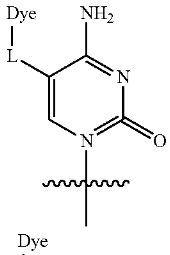

,

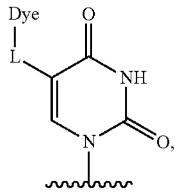

or

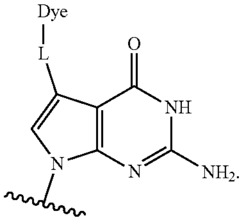

In a particular embodiment, the blocking group is separate and independent of the dye moiety, i.e., not attached to it. Alternatively, the dye may comprise all or part of the 3'-OH blocking group. Thus R''' can be a 3' OH blocking group which may or may not comprise the dye moiety.

In yet another alternative embodiment, there is no blocking group on the 3' carbon of the pentose sugar and the dye (or dye and linker construct) attached to the base, for example, can be of a size or structure sufficient to act as a block to the incorporation of a further nucleotide. Thus, the block can be due to steric hindrance or can be due to a combination of size, charge and structure, whether or not the dye is attached to the 3' position of the sugar.

In still yet another alternative embodiment, the blocking group is present on the 2' or 4' carbon of the pentose sugar and can be of a size or structure sufficient to act as a block to the incorporation of a further nucleotide.

The use of a blocking group allows polymerization to be controlled, such as by stopping extension when a labeled nucleotide is incorporated. If the blocking effect is reversible, for example, by way of non-limiting example by changing chemical conditions or by removal of a chemical block, extension can be stopped at certain points and then allowed to continue.

In a particular embodiment, the linker L (between dye and nucleotide) and blocking group are both present and are separate moieties. In particular embodiments, the linker and blocking group are both cleavable under the same or substantially similar conditions. Thus, deprotection and deblocking processes may be more efficient because only a single treatment will be required to remove both the dye compound and the blocking group. However, in some embodiments a linker and blocking group need not be cleavable under similar conditions, instead being individually cleavable under distinct conditions.

Linkers

The detectable label such as a fluorescent dye may include a reactive linker group at one of the substituent positions for covalent attachment of the compound to a substrate or another molecule. Reactive linking groups are moieties capable of forming a bond (e.g., a covalent or non-covalent bond), in particular a covalent bond. In a particular embodiment the linker may be a cleavable linker. Use of the term "cleavable linker" is not meant to imply that the whole linker is required to be removed. The cleavage site can be located at a position on the linker that ensures that part of the linker remains attached to the dye and/or substrate moiety after cleavage. Cleavable linkers may be, by way of non-limiting example, electrophilically cleavable linkers, nucleophilically cleavable linkers, photocleavable linkers, cleavable under reductive conditions (for example disulfide or azide containing linkers), oxidative conditions, cleavable via use of safety-catch linkers and cleavable by elimination mechanisms. The use of a cleavable linker to attach the dye compound to a substrate moiety ensures that the label can, if required, be removed after detection, avoiding any interfering signal in downstream steps.

Useful linker groups may be found in PCT Publication No. WO2004/018493 (herein incorporated by reference), examples of which include linkers that may be cleaved using water-soluble phosphines or water-soluble transition metal catalysts formed from a transition metal and at least partially water-soluble ligands. In aqueous solution the latter form at least partially water-soluble transition metal complexes. Such cleavable linkers can be used to connect bases of nucleotides to labels such as the dyes set forth herein.

Particular linkers include those disclosed in PCT Publication No. WO2004/018493 (herein incorporated by reference) such as those that include moieties of the formulae:

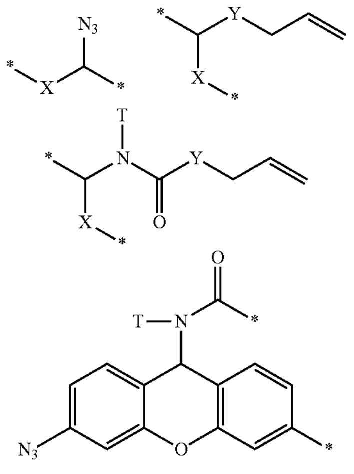

(wherein X is selected from the group comprising O, S, NH and NQ wherein Q is a C1-10 substituted or unsubstituted alkyl group, Y is selected from the group comprising O, S, NH and N(allyl), T is hydrogen or a $C_1$-$C_{10}$ substituted or unsubstituted alkyl group and * indicates where the moiety is connected to the remainder of the nucleotide or nucleoside). In some aspect, the linkers connect the bases of nucleotides to labels such as, for example, the dye compounds described herein.

Additional examples of linkers include those disclosed in U.S. Publication No. 2016/0040225 (herein incorporated by reference), such as those include moieties of the formulae:

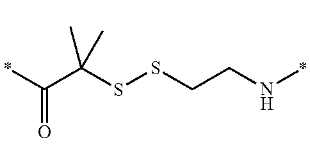
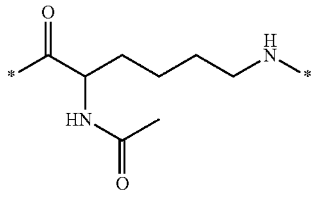
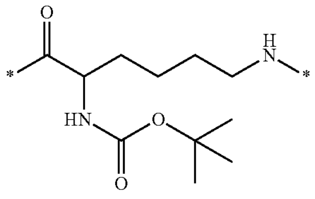
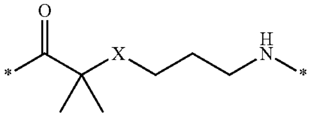

X = $CH_2$, O, S

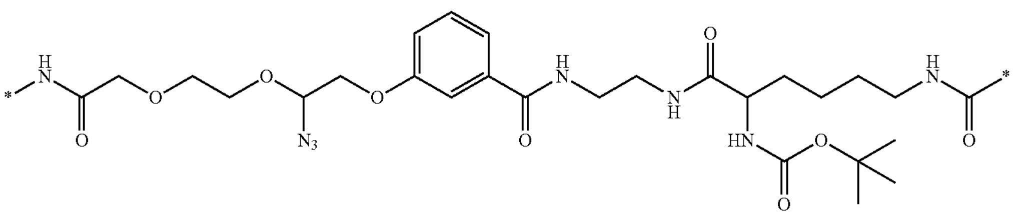

(wherein * indicates where the moiety is connected to the remainder of the nucleotide or nucleoside). The linker moieties illustrated herein may comprise the whole or partial linker structure between the nucleotides/nucleosides and the labels. The linker moieties illustrated herein may comprise the whole or partial linker structure between the nucleotides and the labels.

Additional examples of linkers include moieties of the formula:

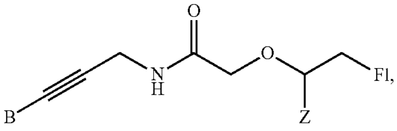,
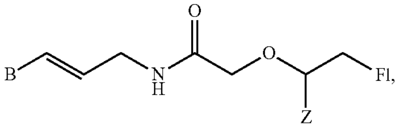,
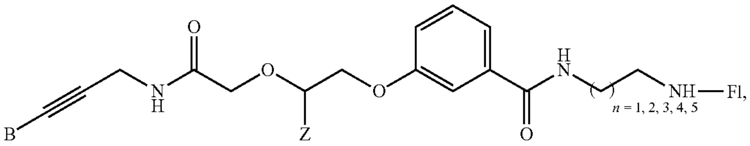,
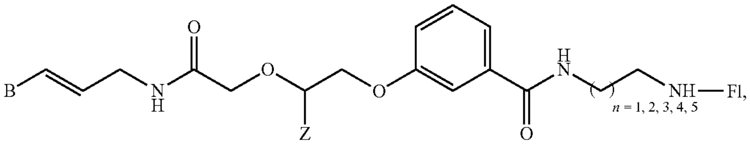,
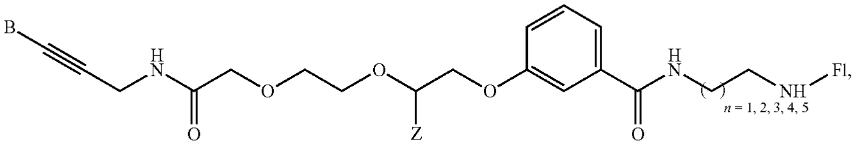, or
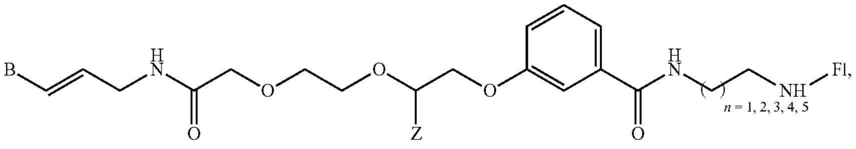, wherein B is a nucleobase; Z is —$N_3$ (azido), —O—$C_1$-$C_6$ alkyl, —O—$C_2$-$C_6$ alkenyl, or —O—$C_2$-$C_6$ alkynyl; and Fl comprises a dye moiety, which may contain additional linker structure. One of ordinary skill in the art understands that the dye compound described herein is covalently bounded to the linker by reacting a functional group of the dye compound (e.g., carboxyl) with a functional group of the linker (e.g., amino). In one embodiment, the cleavable linker comprises

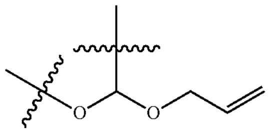 [SMILES: *OC(*)OCC=C]

("AOL" linker moiety) where Z is —O-allyl.

In particular embodiments, the length of the linker between a detectable label and a nucleobase can be altered, for example, by introducing a polyethylene glycol spacer group, thereby increasing the fluorescence intensity compared to the same fluorophore attached to the guanine base through other linkages known in the art. Exemplary linkers and their properties are set forth in PCT Publication No. WO2007020457 (herein incorporated by reference).

A dye may be attached to any position on the nucleotide base, for example, through a linker. In particular embodiments, Watson-Crick base pairing can still be carried out for the resulting analog. Particular nucleobase labeling sites include the C5 position of a pyrimidine base or the C7 position of a 7-deaza purine base. As described above a linker group may be used to covalently attach a dye to the nucleoside or nucleotide.

In particular embodiments the labeled nucleotide or oligonucleotide may be enzymatically incorporable and enzymatically extendable. Accordingly, a linker moiety may be of sufficient length to connect the nucleotide to the compound such that the compound does not significantly interfere with the overall binding and recognition of the nucleotide by a nucleic acid replication enzyme. Thus, the linker can also comprise a spacer unit. The spacer distances, for example, the nucleotide base from a cleavage site or label.

Non-limiting exemplary labeled nucleotides as described herein include:

A

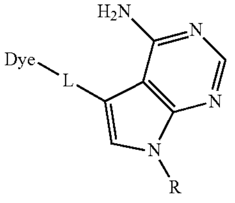

C

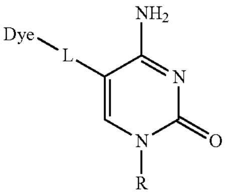

T

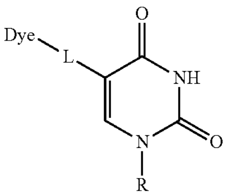

-continued

G

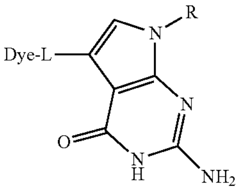

A

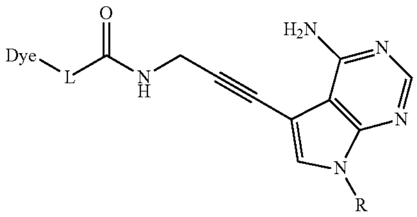

C

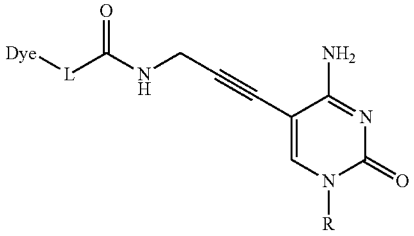

T

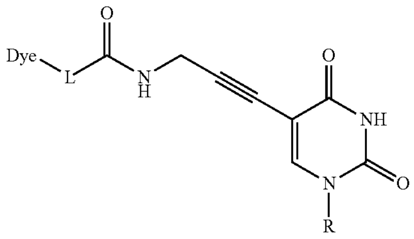

G

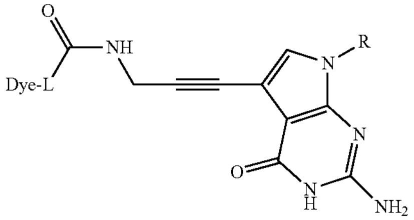

A

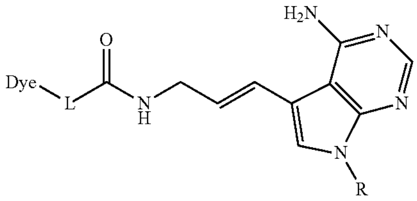

C

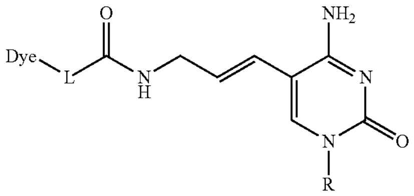

-continued
T
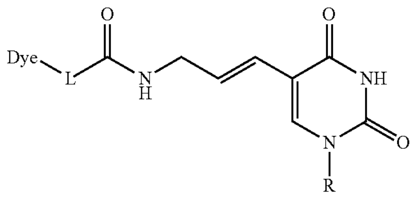
-continued
G
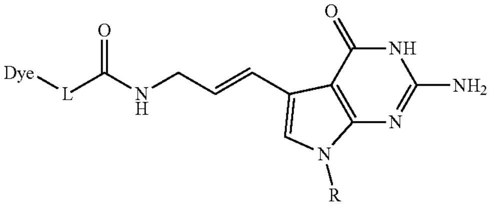
wherein L represents a linker and R represents a ribose or deoxyribose moiety as described above, or a ribose or 2' deoxyribose moiety with the 5' position substituted with mono-, di- or tri-phosphates.
In some embodiments, non-limiting exemplary fluorescent dye conjugates are shown below:
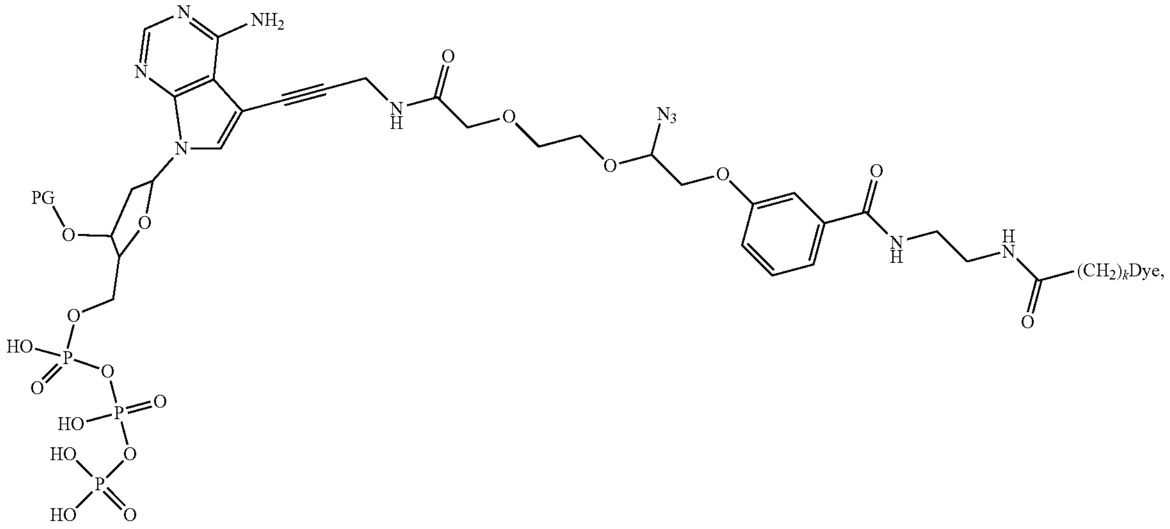
ffA-LN3-Dye
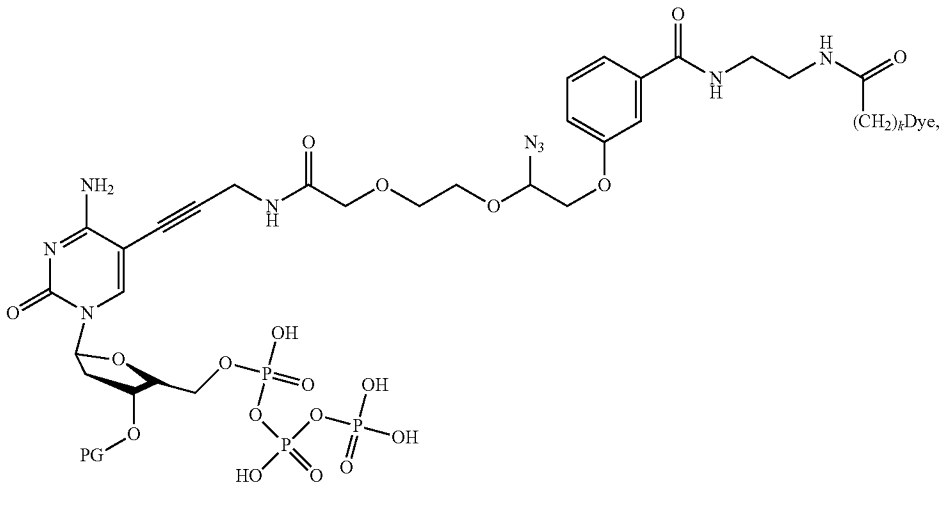
ffC-LN3-Dye -continued
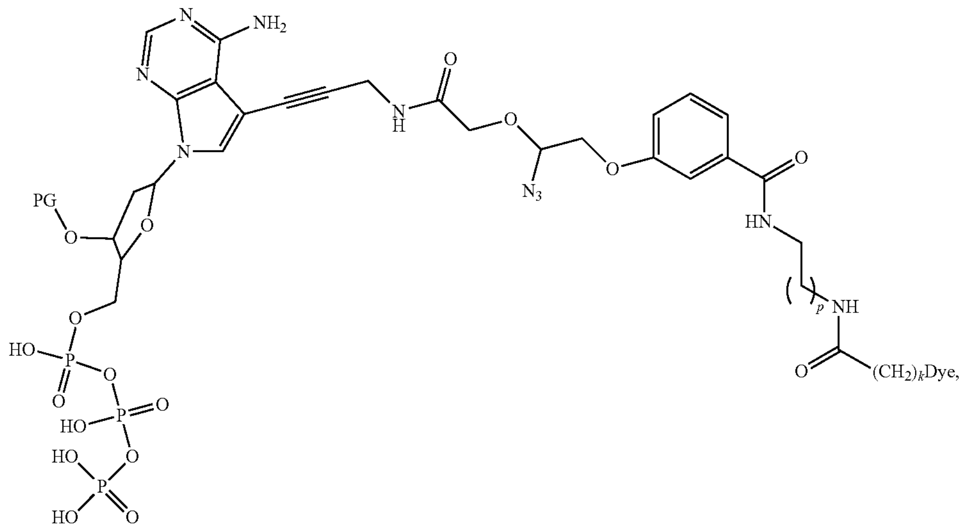
ffA-sPA-LN3-Dye
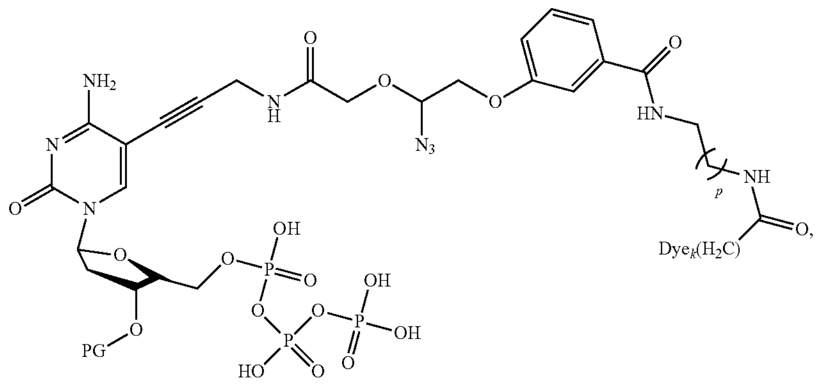
ffC-sPA-LN3-Dye
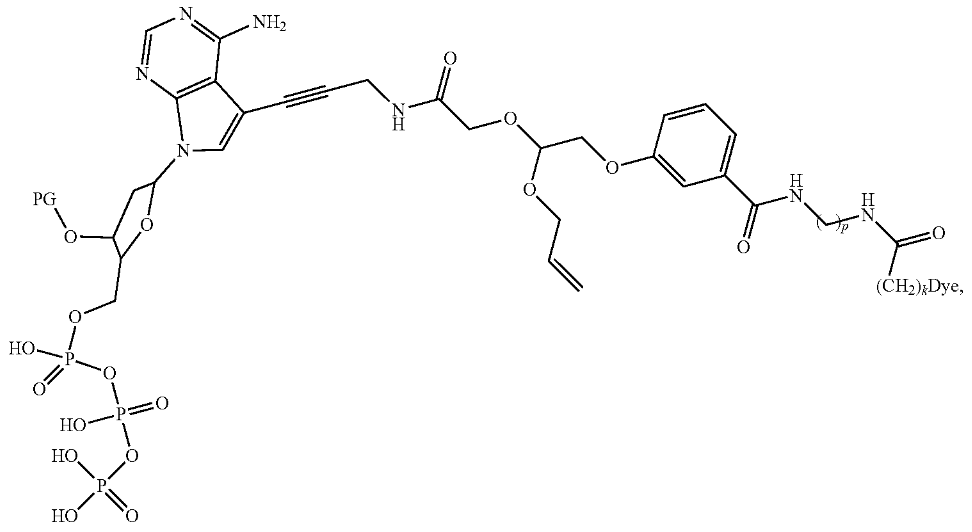
ffA-AOL-Dye -continued
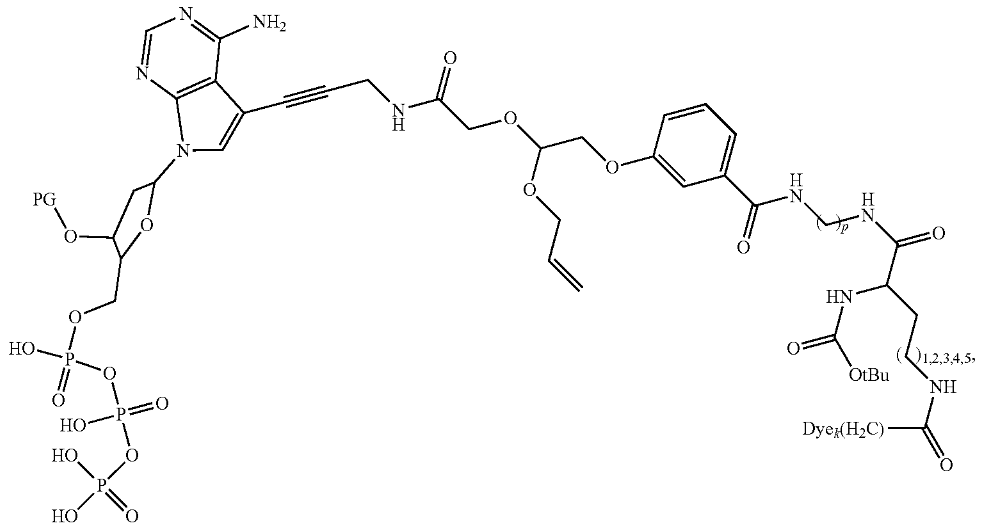
ffA-AOL-BL-Dye
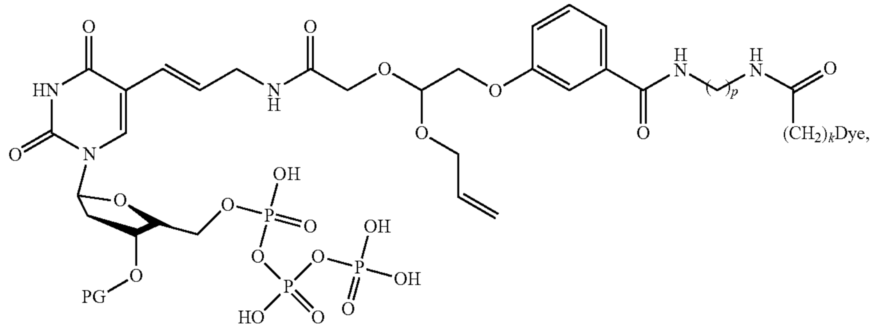
ffT-DB-AOL-Dye
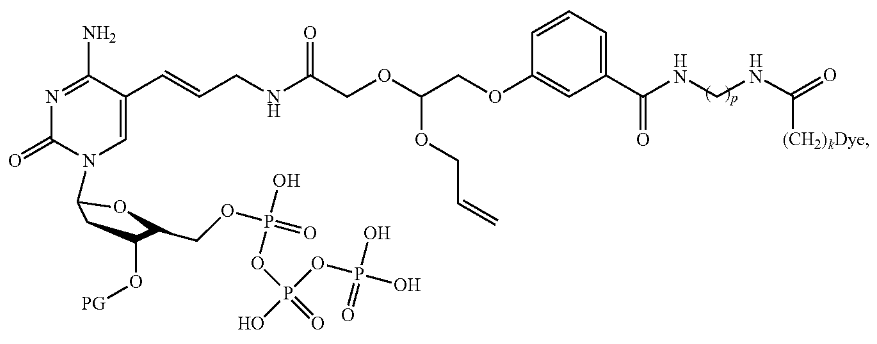
ffC-DB-AOL-Dye -continued

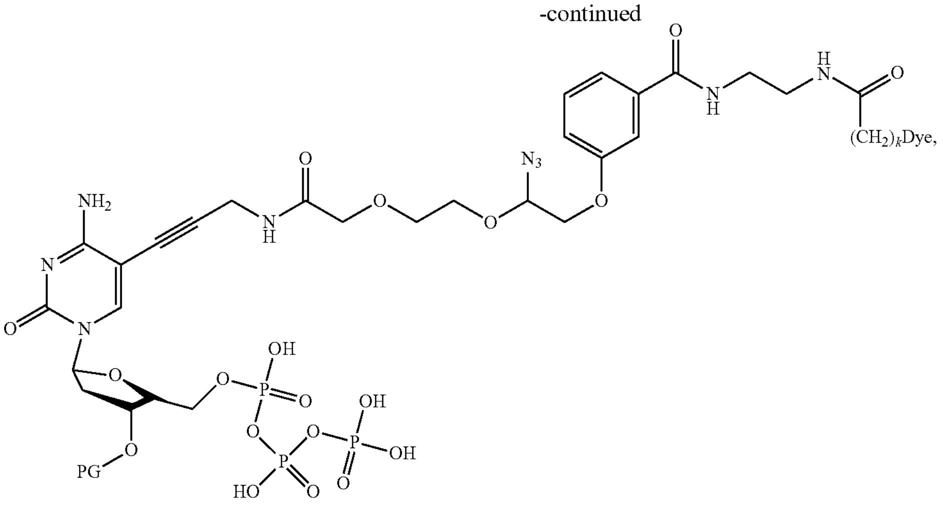

ffC-LN3-Dye wherein PG stands for the 3' OH blocking groups described herein; p is an integer of 1, 2, 3, 4, 5, 6, 7, 8, 9, or 10; and k is 0, 1, 2, 3, 4, or 5. In one embodiment, —O-PG is (AOM)

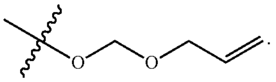

In another embodiment, —O-PG is —O-azidomethyl (AZM). In one embodiment, k is 5. In some further embodiments, p is 1, 2 or 3; and k is 5.

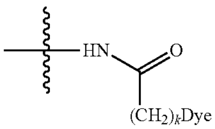

refers to the connection point of the Dye with the cleavable linker as a result of a reaction between an amino group of the linker moiety and the carboxyl group of the Dye. In any embodiments of the labeled nucleotide described herein, the nucleotide is a nucleotide triphosphate.

Various fluorescent dyes may be used in the present disclosure as detectable labels, in particularly those dyes that may be excitation by a blue light (e.g., about 450 nm to about 460 nm) or a green light (e.g., about 520 nm to about 540 nm). These dyes may also be referred to as "blue dyes" and "green dyes" respectively. Examples of various type of blue dyes, including but not limited to coumarin dyes, chromenoquinoline dyes, and bisboron containing heterocycles are disclosed in U.S. Publication Nos. 2018/0094140, 2018/0201981, 2020/0277529, 2020/0277670, 2021/0188832, 2022/0195517 A1, 2022/0380389 A1 and U.S. Ser. No. 63/325,057, each of which is incorporated by reference in its entirety. Examples of green dyes including cyanine or polymethine dyes disclosed in International Publication Nos. WO2013/041117, WO2014/135221, WO 2016/189287, WO2017/051201 and WO2018/060482A1, each of which is incorporated by reference in its entirety.

3' Blocking Groups

The labeled nucleotide may also have a blocking group covalently attached to the ribose or deoxyribose sugar of the nucleotide. The blocking group may be attached at any position on the ribose or deoxyribose sugar. In particular embodiments, the blocking group is at the 3' OH position of the ribose or deoxyribose sugar of the nucleotide. Various 3' OH blocking group are disclosed in WO2004/018497 and WO2014/139596, which are hereby incorporated by references. For example, the blocking group may be azidomethyl ($—CH_2N_3$) or substituted azidomethyl (e.g., $—CH(CHF_2)N_3$ or $CH(CH_2F)N_3$), or allyl connecting to the 3' oxygen atom of the ribose or deoxyribose moiety. In some embodiments, the 3' blocking group is azidomethyl, forming $3'-OCH_2N_3$ with the 3' carbon of the ribose or deoxyribose.

Additional 3' blocking groups are disclosed in U.S. Publication No. 2020/0216891 A1, which is incorporated by reference in its entirety. Non-limiting examples of the 3' blocking group include:

(AOM)

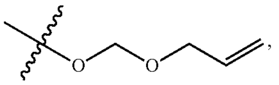

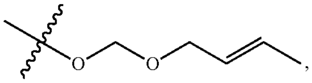

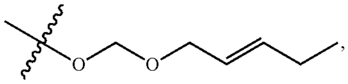

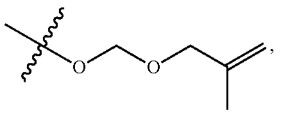

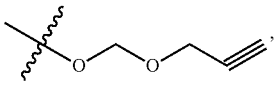

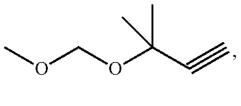

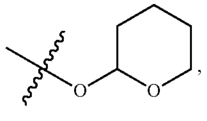

and

-continued

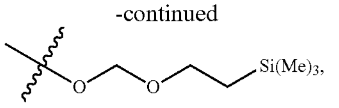

each covalently attached to the 3' carbon of the ribose or deoxyribose.

Cleavage Mixture for Deprotection of the 3' Blocking Groups

In some embodiments, the 3' blocking group such as azidomethyl may be removed or deprotected by a chemical reagent to generate a free hydroxy group, for example, in the presence of a water soluble phosphine reagent. Non-limiting examples include tris(hydroxymethyl)phosphine (THMP), tris(hydroxyethyl)phosphine (THEP) or tris(hydroxylpropyl)phosphine (THP or THPP). 3'-acetal blocking groups described herein may be removed or cleaved under various chemical conditions. For 3' acetal blocking groups such as

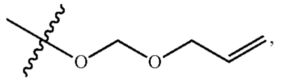 [SMILES: *OCOCC=C]

non-limiting cleaving condition includes a Pd(II) complex, such as $Pd(OAc)_2$ or allylPd(II) chloride dimer, in the presence of a phosphine ligand, for example tris(hydroxymethyl)phosphine (THMP), or tris(hydroxylpropyl)phosphine (THP or THPP). For those blocking groups containing an alkynyl group (e.g., an ethynyl), they may also be removed by a Pd(II) complex (e.g., $Pd(OAc)_2$ or allyl Pd(II) chloride dimer) in the presence of a phosphine ligand (e.g., THP or THMP).

Palladium Cleavage Reagents

In some embodiments, the 3' blocking group such as allyl or AOM as described herein may be cleaved by a palladium catalyst. In some such embodiments, the Pd catalyst is water soluble. In some such embodiments, is a Pd(0) complex (e.g., Tris(3,3',3"-phosphinidynetris(benzenesulfonato)palladium(0) nonasodium salt nonahydrate). In some instances, the Pd(0) complex may be generated in situ from reduction of a Pd(II) complex by reagents such as alkenes, alcohols, amines, phosphines, or metal hydrides. Suitable palladium sources include $Na_2PdCl_4$, $Li_2PdCl_4$, $Pd(CH_3CN)_2Cl_2$, $(PdCl(C_3H_5))_2$, $[Pd(C_3H_5)(THP)]Cl$, $[Pd(C_3H_5)(THP)_2]Cl$, $Pd(OAc)_2$, $Pd(Ph_3)_4$, $Pd(dba)_2$, $Pd(Acac)_2$, $PdCl_2(COD)$, $Pd(TFA)_2$, $Na_2PdBr_4$, $K_2PdBr_4$, $PdCl_2$, $PdBr_2$, and $Pd(NO_3)_2$. In one such embodiment, the Pd(0) complex is generated in situ from $Na_2PdCl_4$ or $K_2PdCl_4$. In another embodiment, the palladium source is allyl palladium(II) chloride dimer $[(PdCl(C_3H_5))_2]$. In some embodiments, the Pd(0) complex is generated in an aqueous solution by mixing a Pd(II) complex with a phosphine. Suitable phosphines include water soluble phosphines, such as THP, THMP, PTA, TCEP, bis(p-sulfonatophenyl)phenylphosphine dihydrate potassium salt, or triphenylphosphine-3,3',3"-trisulfonic acid trisodium salt.

In some embodiments, the palladium catalyst is prepared by mixing $[(Allyl)PdCl]_2$ with THP in situ. The molar ratio of $[(Allyl)PdCl]_2$ and the THP may be about 1:1, 1:1.5, 1:2, 1:2.5, 1:3, 1:3.5, 1:4, 1:4.5, 1:5, 1:5.5, 1:6, 1:6.5, 1:7, 1:7.5, 1:8, 1:8.5, 1:9, 1:9.5 or 1:10. In one embodiment, the molar ratio of $[(Allyl)PdCl]_2$ to THP is 1:10. In some other embodiment, the palladium catalyst is prepared by mixing a water soluble Pd reagent such as $Na_2PdCl_4$ or $K_2PdCl_4$ with THP in situ. The molar ratio of $Na_2PdCl_4$ or $K_2PdCl_4$ and THP may be about 1:1, 1:1.5, 1:2, 1:2.5, 1:3, 1:3.5, 1:4, 1:4.5, 1:5, 1:5.5, 1:6, 1:6.5, 1:7, 1:7.5, 1:8, 1:8.5, 1:9, 1:9.5 or 1:10. In one embodiment, the molar ratio of $Na_2PdCl_4$ or $K_2PdCl_4$ to THP is about 1:3. In another embodiment, the molar ratio of $Na_2PdCl_4$ or $K_2PdCl_4$ to THP is about 1:3.5. In yet another embodiment, the molar ratio of $Na_2PdCl_4$ or $K_2PdCl_4$ to THP is about 1:2.5. In some further embodiments, one or more reducing agents may be added, such as ascorbic acid or a salt thereof (e.g., sodium ascorbate). In some embodiments, the cleavage mixture may contain additional buffer reagents, such as a primary amine, a secondary amine, a tertiary amine, a carbonate salt, a phosphate salt, or a borate salt, or combinations thereof. In some further embodiments, the buffer reagent comprises ethanolamine (EA), tris(hydroxymethyl)aminomethane (Tris), glycine, sodium carbonate, sodium phosphate, sodium borate, 2-dimethylethanolamine (DMEA), 2-diethylethanolamine (DEEA), N,N,N',N'-tetramethylethylenediamine (TEMED), N,N,N',N'-tetraethylethylenediamine (TEEDA), or 2-piperidine ethanol (also known as (2-hydroxyethyl)piperidine, having the structure

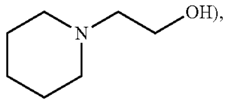

or combinations thereof. In one embodiment, the buffer reagent comprises or is DEEA. In another embodiment, the buffer reagent comprises or is (2-hydroxyethyl)piperidine. In another embodiment, the buffer reagent contains one or more inorganic salts such as a carbonate salt, a phosphate salt, or a borate salt, or combinations thereof. In one embodiment, the inorganic salt is a sodium salt.

Methods of Sequencing

Some embodiments of the present application are directed to a method for determining the sequences of a plurality of different target polynucleotides, comprising:

(a) contacting a solid support with a solution comprising sequencing primers under hybridization conditions, wherein the solid support comprises a plurality of different target polynucleotides immobilized thereon; and the sequencing primers are complementary to at least a portion of the target polynucleotides;

(b) contacting the solid support with an aqueous solution comprising DNA polymerase and one more of four different types of nucleotides (e.g., dATP, dGTP, dCTP and dTTP or dUTP), under conditions suitable for DNA polymerase-mediated primer extension, and incorporating one type of nucleotides into the sequencing primers to produce extended copy polynucleotides, wherein at least one type of nucleotide is a labeled nucleotide described herein, and wherein each of the four types of nucleotides comprises a 3' blocking group;

(c) imaging the solid support and performing one or more fluorescent measurements of the extended copy polynucleotides; and (d) removing the 3' blocking group of the incorporated nucleotides. In some embodiments, step (d) also removes the labels of the incorporated nucleotides (if the incorporated nucleotides are labeled). In some such embodiments, the labels and the 3' blocking groups of the incorporated nucleotides are removed in a single chemical reaction. In some further embodiments, the method may also comprises (e) washing the solid support with an aqueous wash solution (e.g., washing the removed label moiety and the 3' blocking group away from the extended copy polynucleotides). In some embodiments, steps (b) through (e) are repeated at least 30, 40, 50, 60, 70, 80, 90, 100, 110, 120, 130, 140, 150, 160, 170, 180, 190, 200, 250, 300, 350, 400, 450 or 500 cycles to determine the target polynucleotide sequences. In some embodiments, the four types of nucleotides comprise dATP, dCTP, dGTP and dTTP or dUTP, or non-natural nucleotide analogs thereof. In some embodiments, the sequence determination is conducted after the completion of repeated cycles of the sequencing steps described herein.

In some further embodiments, the method is performed on an automated sequencing instrument, and wherein the automated sequencing instrument comprises a single light source operating with a blue laser at about 450 nm to about 460 nm. The incorporation of the first type of the nucleotide is determined by detection in the one of the blue or green channel/region (e.g., at a blue region with a wavelength ranging from about 472 to about 520 nm, or at a green region with a wavelength ranging from about 540 nm to about 640 nm). The incorporation of the second type of nucleotide is determined by detection in the other one of the blue or green detection channel/region. The incorporation of the third type of nucleotide is determined by detection in both the blue and green channels/regions. The incorporation of the fourth type of nucleotide is determined by no detection in either the blue or the green channel/region.

In other embodiments, the automatic sequencing instrument may comprise two light sources operating at different wavelengths (e.g., at 450-460 nm and 520-530 nm). The incorporation of the first type of the nucleotide conjugates is determined by a signal state in the first imaging event and a dark state in the second imaging event. The incorporation of the second type of the nucleotide conjugates is determined by a dark state in the first imaging event and a signal state in the second imaging event. The incorporation of the third type of the nucleotide conjugates is determined by a signal state in both the first imaging event and the second imaging event. The incorporation of the fourth type of the nucleotide conjugates is determined by a dark state in both the first imaging event and the second imaging event.

In some embodiments, the target polynucleotide is immobilized on a solid support. In some further embodiments, the solid support comprises an array or a plurality of different immobilized target polynucleotides. In further embodiments, the solid support comprises a patterned flow cell. In further embodiments, the patterned flow cell comprises a plurality of nanowells. In further embodiments, the solid support comprises at least 5,000,000 spatially distinguishable sites/cm2 that comprise multiple copies of target polynucleotides.

In some embodiments, at least one nucleotide is incorporated into a polynucleotide (such as a single stranded primer polynucleotide described herein) in the synthetic step by the action of a polymerase enzyme. However, other methods of joining nucleotides to polynucleotides, such as, for example, chemical oligonucleotide synthesis or ligation of labeled oligonucleotides to unlabeled oligonucleotides, can be used. Therefore, the term "incorporating," when used in reference to a nucleotide and polynucleotide, can encompass polynucleotide synthesis by chemical methods as well as enzymatic methods.

In a specific embodiment, a synthetic step is carried out and may optionally comprise incubating a template or target polynucleotide strand with a reaction mixture comprising fluorescently labeled nucleotides of the disclosure. A polymerase can also be provided under conditions which permit formation of a phosphodiester linkage between a free 3' hydroxyl group on a polynucleotide strand annealed to the template or target polynucleotide strand and a 5' phosphate group on the labeled nucleotide. Thus, a synthetic step can include formation of a polynucleotide strand as directed by complementary base pairing of nucleotides to a template/target strand.

In all embodiments of the methods, the detection step may be carried out while the polynucleotide strand into which the labeled nucleotides are incorporated is annealed to a template/target strand, or after a denaturation step in which the two strands are separated. Further steps, for example chemical or enzymatic reaction steps or purification steps, may be included between the synthetic step and the detection step. In particular, the polynucleotide strand incorporating the labeled nucleotide(s) may be isolated or purified and then processed further or used in a subsequent analysis. By way of example, polynucleotide strand incorporating the labeled nucleotide(s) as described herein in a synthetic step may be subsequently used as labeled probes or primers. In other embodiments, the product of the synthetic step set forth herein may be subject to further reaction steps and, if desired, the product of these subsequent steps purified or isolated.

Suitable conditions for the synthetic step will be well known to those familiar with standard molecular biology techniques. In one embodiment, a synthetic step may be analogous to a standard primer extension reaction using nucleotide precursors, including the labeled nucleotides as described herein, to form an extended polynucleotide strand (primer polynucleotide strand) complementary to the template/target strand in the presence of a suitable polymerase enzyme. In other embodiments, the synthetic step may itself form part of an amplification reaction producing a labeled double stranded amplification product comprised of annealed complementary strands derived from copying of the primer and template polynucleotide strands. Other exemplary synthetic steps include nick translation, strand displacement polymerization, random primed DNA labeling, etc. A particularly useful polymerase enzyme for a synthetic step is one that is capable of catalyzing the incorporation of the labeled nucleotides as set forth herein. A variety of naturally occurring or mutant/modified polymerases can be used. By way of example, a thermostable polymerase can be used for a synthetic reaction that is carried out using thermocycling conditions, whereas a thermostable polymerase may not be desired for isothermal primer extension reactions. Suitable thermostable polymerases which are capable of incorporating the labeled nucleotides according to the disclosure include those described in WO 2005/024010 or WO06120433, each of which is incorporated herein by reference. In synthetic reactions which are carried out at lower temperatures such as 37° C., polymerase enzymes need not necessarily be thermostable polymerases, therefore the choice of polymerase will depend on a number of factors such as reaction temperature, pH, strand-displacing activity and the like.

In specific non-limiting embodiments, the disclosure encompasses methods of nucleic acid sequencing, re-sequencing, whole genome sequencing, single nucleotide polymorphism scoring, any other application involving the detection of the modified nucleotide or nucleoside labeled with dyes set forth herein when incorporated into a polynucleotide.

A particular embodiment of the disclosure provides use of labeled nucleotides comprising dye moiety according to the disclosure in a polynucleotide sequencing-by-synthesis reaction. Sequencing-by-synthesis generally involves sequential addition of one or more nucleotides or oligonucleotides to a growing polynucleotide chain in the 5' to 3' direction using a polymerase or ligase in order to form an extended polynucleotide chain complementary to the template/target nucleic acid to be sequenced. The identity of the base present in one or more of the added nucleotide(s) can be determined in a detection or "imaging" step. The identity of the added base may be determined after each nucleotide incorporation step. The sequence of the template may then be inferred using conventional Watson-Crick base-pairing rules. The use of the nucleotides labeled with dyes set forth herein for determination of the identity of a single base may be useful, for example, in the scoring of single nucleotide polymorphisms, and such single base extension reactions are within the scope of this disclosure.

In an embodiment of the present disclosure, the sequence of a template/target polynucleotide is determined by detecting the incorporation of one or more nucleotides into a nascent strand complementary to the template polynucleotide to be sequenced through the detection of fluorescent label(s) attached to the incorporated nucleotide(s). Sequencing of the template polynucleotide can be primed with a suitable primer (or prepared as a hairpin construct which will contain the primer as part of the hairpin), and the nascent chain is extended in a stepwise manner by addition of nucleotides to the 3' end of the primer in a polymerase-catalyzed reaction.

In particular embodiments, each of the different nucleotide triphosphates (A, T, G and C) may be labeled with a unique fluorophore and also comprises a blocking group at the 3' position to prevent uncontrolled polymerization. Alternatively, one of the four nucleotides may be unlabeled (dark). The polymerase enzyme incorporates a nucleotide into the nascent chain complementary to the template/target polynucleotide, and the blocking group prevents further incorporation of nucleotides. Any unincorporated nucleotides can be washed away and the fluorescent signal from each incorporated nucleotide can be "read" optically by suitable means, such as a charge-coupled device using light source excitation and suitable emission filters. The 3' blocking group and fluorescent dye compounds can then be removed (deprotected) (simultaneously or sequentially) to expose the nascent chain for further nucleotide incorporation. Typically, the identity of the incorporated nucleotide will be determined after each incorporation step, but this is not strictly essential. Similarly, U.S. Pat. No. 5,302,509 (which is incorporated herein by reference) discloses a method to sequence polynucleotides immobilized on a solid support.

The method, as exemplified above, utilizes the incorporation of fluorescently labeled, 3'-blocked nucleotides A, G, C, and T into a growing strand complementary to the immobilized polynucleotide, in the presence of DNA polymerase. The polymerase incorporates a base complementary to the target polynucleotide but is prevented from further addition by the 3'-blocking group. The label of the incorporated nucleotide can then be determined, and the blocking group removed by chemical cleavage to allow further polymerization to occur. The nucleic acid template to be sequenced in a sequencing-by-synthesis reaction may be any polynucleotide that it is desired to sequence. The nucleic acid template for a sequencing reaction will typically comprise a double stranded region having a free 3' hydroxyl group that serves as a primer or initiation point for the addition of further nucleotides in the sequencing reaction. The region of the template to be sequenced will overhang this free 3' hydroxyl group on the complementary strand. The overhanging region of the template to be sequenced may be single stranded but can be double-stranded, provided that a "nick is present" on the strand complementary to the template strand to be sequenced to provide a free 3' OH group for initiation of the sequencing reaction. In such embodiments, sequencing may proceed by strand displacement. In certain embodiments, a primer bearing the free 3' hydroxyl group may be added as a separate component (e.g., a short oligonucleotide) that hybridizes to a single-stranded region of the template to be sequenced. Alternatively, the primer and the template strand to be sequenced may each form part of a partially self-complementary nucleic acid strand capable of forming an intra-molecular duplex, such as for example a hairpin loop structure. Hairpin polynucleotides and methods by which they may be attached to solid supports are disclosed in PCT Publication Nos. WO0157248 and WO2005/047301, each of which is incorporated herein by reference. Nucleotides can be added successively to a growing primer, resulting in synthesis of a polynucleotide chain in the 5' to 3' direction. The nature of the base which has been added may be determined, particularly but not necessarily after each nucleotide addition, thus providing sequence information for the nucleic acid template. Thus, a nucleotide is incorporated into a nucleic acid strand (or polynucleotide) by joining of the nucleotide to the free 3' hydroxyl group of the nucleic acid strand via formation of a phosphodiester linkage with the 5' phosphate group of the nucleotide.

The nucleic acid template to be sequenced may be DNA or RNA, or even a hybrid molecule comprised of deoxynucleotides and ribonucleotides. The nucleic acid template may comprise naturally occurring and/or non-naturally occurring nucleotides and natural or non-natural backbone linkages, provided that these do not prevent copying of the template in the sequencing reaction.

In certain embodiments, the nucleic acid template to be sequenced may be attached to a solid support via any suitable linkage method known in the art, for example via covalent attachment. In certain embodiments template polynucleotides may be attached directly to a solid support (e.g., a silica-based support). However, in other embodiments of the disclosure the surface of the solid support may be modified in some way so as to allow either direct covalent attachment of template polynucleotides, or to immobilize the template polynucleotides through a hydrogel or polyelectrolyte multilayer, which may itself be non-covalently attached to the solid support.

Arrays in which polynucleotides have been directly attached to a support (for example, silica-based supports such as those disclosed in WO00/06770 (incorporated herein by reference), wherein polynucleotides are immobilized on a glass support by reaction between a pendant epoxide group on the glass with an internal amino group on the polynucleotide. In addition, polynucleotides can be attached to a solid support by reaction of a sulfur-based nucleophile with the solid support, for example, as described in WO2005/047301 (incorporated herein by reference). A still further example of solid-supported template polynucleotides is where the template polynucleotides are attached to hydrogel supported upon silica-based or other solid supports, for example, as described in WO00/31148, WO01/01143, WO02/12566, WO03/014392, U.S. Pat. No. 6,465,178 and WO00/53812, each of which is incorporated herein by reference.

A particular surface to which template polynucleotides may be immobilized is a polyacrylamide hydrogel. Polyacrylamide hydrogels are described in the references cited above and in WO2005/065814, which is incorporated herein by reference. Specific hydrogels that may be used include those described in WO2005/065814 and U.S. Pub. No. 2014/0079923. In one embodiment, the hydrogel is PAZAM (poly(N-(5-azidoacetamidylpentyl) acrylamide-co-acrylamide)).

DNA template molecules can be attached to beads or microparticles, for example, as described in U.S. Pat. No. 6,172,218 (which is incorporated herein by reference). Attachment to beads or microparticles can be useful for sequencing applications. Bead libraries can be prepared where each bead contains different DNA sequences. Exemplary libraries and methods for their creation are described in Nature, 437, 376-380 (2005); Science, 309, 5741, 1728-1732 (2005), each of which is incorporated herein by reference. Sequencing of arrays of such beads using nucleotides set forth herein is within the scope of the disclosure.

Template(s) that are to be sequenced may form part of an "array" on a solid support, in which case the array may take any convenient form. Thus, the method of the disclosure is applicable to all types of high-density arrays, including single-molecule arrays, clustered arrays, and bead arrays. Nucleotides labeled with dye compounds of the present disclosure may be used for sequencing templates on essentially any type of array, including but not limited to those formed by immobilization of nucleic acid molecules on a solid support.

However, nucleotides labeled with dye compounds of the disclosure are particularly advantageous in the context of sequencing of clustered arrays. In clustered arrays, distinct regions on the array (often referred to as sites, or features) comprise multiple polynucleotide template molecules. Generally, the multiple polynucleotide molecules are not individually resolvable by optical means and are instead detected as an ensemble. Depending on how the array is formed, each site on the array may comprise multiple copies of one individual polynucleotide molecule (e.g., the site is homogenous for a particular single- or double-stranded nucleic acid species) or even multiple copies of a small number of different polynucleotide molecules (e.g., multiple copies of two different nucleic acid species). Clustered arrays of nucleic acid molecules may be produced using techniques generally known in the art. By way of example, WO 98/44151 and WO00/18957, each of which is incorporated herein, describe methods of amplification of nucleic acids wherein both the template and amplification products remain immobilized on a solid support in order to form arrays comprised of clusters or "colonies" of immobilized nucleic acid molecules. The nucleic acid molecules present on the clustered arrays prepared according to these methods are suitable templates for sequencing using nucleotides labeled with dye compounds of the disclosure.

Nucleotides labeled with dye compounds of the present disclosure are also useful in sequencing of templates on single molecule arrays. The term "single molecule array" or "SMA" as used herein refers to a population of polynucleotide molecules, distributed (or arrayed) over a solid support, wherein the spacing of any individual polynucleotide from all others of the population is such that it is possible to individually resolve the individual polynucleotide molecules. The target nucleic acid molecules immobilized onto the surface of the solid support can thus be capable of being resolved by optical means in some embodiments. This means that one or more distinct signals, each representing one polynucleotide, will occur within the resolvable area of the particular imaging device used.

Single molecule detection may be achieved wherein the spacing between adjacent polynucleotide molecules on an array is at least 100 nm, more particularly at least 250 nm, still more particularly at least 300 nm, even more particularly at least 350 nm. Thus, each molecule is individually resolvable and detectable as a single molecule fluorescent point, and fluorescence from said single molecule fluorescent point also exhibits single step photobleaching.

The terms "individually resolved" and "individual resolution" are used herein to specify that, when visualized, it is possible to distinguish one molecule on the array from its neighboring molecules. Separation between individual molecules on the array will be determined, in part, by the particular technique used to resolve the individual molecules. The general features of single molecule arrays will be understood by reference to published applications WO00/06770 and WO 01/57248, each of which is incorporated herein by reference. Although one use of the labeled nucleotides of the disclosure is in sequencing-by-synthesis reactions, the utility of such nucleotides is not limited to such methods. In fact, the labeled nucleotides described herein may be used advantageously in any sequencing methodology which requires detection of fluorescent labels attached to nucleotides incorporated into a polynucleotide.

In particular, nucleotides labeled with dye compounds of the disclosure may be used in automated fluorescent sequencing protocols, particularly fluorescent dye-terminator cycle sequencing based on the chain termination sequencing method of Sanger and co-workers. Such methods generally use enzymes and cycle sequencing to incorporate fluorescently labeled dideoxynucleotides in a primer extension sequencing reaction. So-called Sanger sequencing methods, and related protocols (Sanger-type), utilize randomized chain termination with labeled dideoxynucleotides.

Thus, the present disclosure also encompasses nucleotides labeled with dye compounds which are dideoxynucleotides lacking hydroxyl groups at both of the 3' and 2' positions, such modified dideoxynucleotides being suitable for use in Sanger type sequencing methods and the like.

Nucleotides labeled with dye compounds of the present disclosure incorporating 3' blocking groups, it will be recognized, may also be of utility in Sanger methods and related protocols since the same effect achieved by using dideoxy nucleotides may be achieved by using nucleotides having 3' OH blocking groups: both prevent incorporation of subsequent nucleotides. Where nucleotides according to the present disclosure, and having a 3' blocking group are to be used in Sanger-type sequencing methods it will be appreciated that the dye compounds or detectable labels attached to the nucleotides need not be connected via cleavable linkers, since in each instance where a labeled nucleotide of the disclosure is incorporated; no nucleotides need to be subsequently incorporated and thus the label need not be removed from the nucleotide.

Alternatively, the sequencing methods described herein may also be carried out using unlabeled nucleotides and affinity reagents containing a fluorescent dye described herein. For example, one, two, three or each of the four different types of nucleotides (e.g., dATP, dCTP, dGTP and dTTP or dUTP) in the incorporation mixture of step (a) may be unlabeled. Each of the four types of nucleotides (e.g., dNTPs) has a 3' blocking group to ensure that only a single base can be added by a polymerase to the 3' end of the primer polynucleotide. After incorporation of an unlabeled nucleotide in step (b), the remaining unincorporated nucleotides are washed away. An affinity reagent is then introduced that specifically recognizes and binds to the incorporated dNTP to provide a labeled extension product comprising the incorporated dNTP. Uses of unlabeled nucleotides and affinity reagents in sequencing by synthesis have been disclosed in WO 2018/129214 and WO 2020/097607. A modified sequencing method of the present disclosure using unlabeled nucleotides may include the following steps:

(a') contacting a solid support with a solution comprising sequencing primers under hybridization conditions, wherein the solid support comprises a plurality of different target polynucleotides immobilized thereon; and the sequencing primers are complementary to at least a portion of the target polynucleotides;

(b') contacting the solid support with an aqueous solution comprising DNA polymerase and one more of four different types of unlabeled nucleotides (e.g., dATP, dCTP, dGTP, and dTTP or dUTP) under conditions suitable for DNA polymerase-mediated primer extension, and incorporating one type of nucleotides into the sequencing primers to produce extended copy polynucleotides, and wherein each of the four types of nucleotides comprises a 3' blocking group;

(c') contacting the extended copy polynucleotides with a set of affinity reagents under conditions wherein one affinity reagent binds specifically to the incorporated unlabeled nucleotides to provide labeled extended copy polynucleotides;

(d') imaging the solid support and performing one or more fluorescent measurements of the extended copy polynucleotides; and (e') removing the 3' blocking group of the incorporated nucleotides.

In some embodiments of the modified sequencing method described herein, the method further comprises removing the affinity reagents from the incorporated nucleotides. In still further embodiments, the 3' blocking group and the affinity reagent are removed in the same reaction. In some embodiments, the method further comprises a step (f') washing the solid support with an aqueous wash solution. In further embodiments, steps (b') through (f') are repeated at least 50, 100, 150, 200, 250, 300, 350, 400, 450 or 500 cycles to determine the target polynucleotide sequences. In some embodiments, the set of affinity reagents may comprise a first affinity reagent that binds specifically to the first type of nucleotide, a second affinity reagent that binds specifically to the second type of nucleotide, and a third affinity reagent that binds specifically to the third type of nucleotide. In some further embodiments, each of the first, second and the third affinity reagents comprises a detectable labeled that is spectrally distinguishable. In some embodiments, the affinity reagents may include protein tags, antibodies (including but not limited to binding fragments of antibodies, single chain antibodies, bispecific antibodies, and the like), aptamers, knottins, affimers, or any other known agent that binds an incorporated nucleotide with a suitable specificity and affinity. In one embodiment, at least one affinity reagent is an antibody or a protein tag. In another embodiment, at least one of the first type, the second type, and the third type of affinity reagents is an antibody or a protein tag comprising one or more detectable labels (e.g., multiple copies of the same detectable label). The aqueous scan mixture and the kits described herein may also be used in the modified sequencing method, for example step (d').

EXAMPLES

Additional embodiments are disclosed in further detail in the following examples, which are not in any way intended to limit the scope of the claims.

Example 1. Sequencing by Synthesis on NovaSeg™ Blue/Green Two-Channel System In this experiment, a new scan mix was tested on an Illumina NovaSeg™ breadboard instrument with blue and green laser imaging system, which was set up to take a first image with a blue excitation light (~450 nm) and a second image with a green excitation light (~520 nm) used a ramping laser power setting between 864 mW to 1954 mW (100%, 1× scale) or between 1037 mW to 2345 mW (120%, 1.2× scale) in both blue and green channels. The incorporation mix contained the following ffNs: Green ffT (LN3-AF550POPOS0), Dark G, Red ffC (LN3-507181), Blue ffC (sPA-coumarin blue dye A), Blue ffA (LN3-BL-blue coumarin dye B), Green ffA (LN3-BL-NR550SO). Coumarin dye A is disclosed in U.S. Publication No. 2022/0033900 A1, having the structure moiety

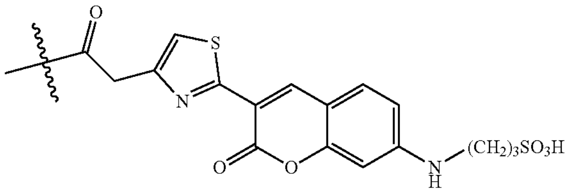

when conjugated with ffC. Coumarin dye B is disclosed in U.S. Publication No. 2020/0277670 A1, having the structure moiety

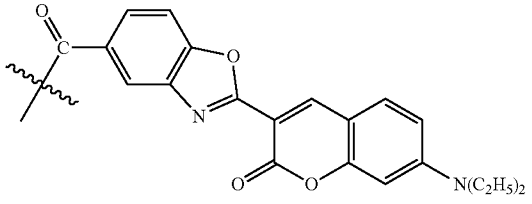

when conjugated with the ffA. AF550POPOS0 is disclosed in U.S. Publication No. 2018/0282791 A1, having the structure moiety

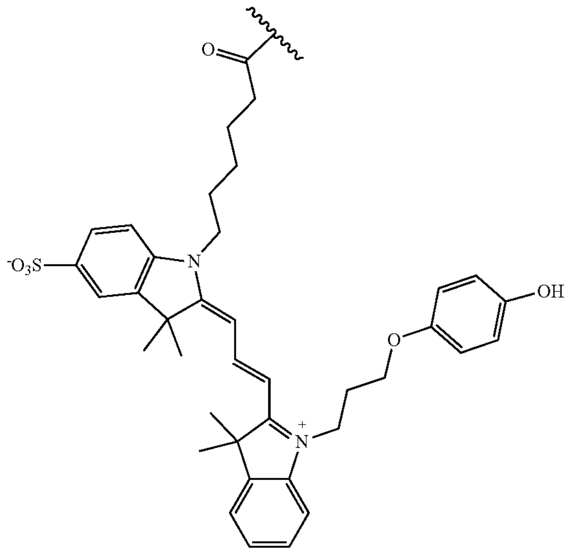

when conjugated with the ffT.

The scan mixes used in the experiments were: 1) a standard scan mix (VSM) contains the following: 1M Tris buffer (pH 7.5), 20 mM sodium ascorbate, 10 mM HEG and 0.05% Tween 20; 2) a new scan mixture (MTC) for reducing signal decay contains the following: 1M Tris buffer (pH 7.5), 10 mM HEG, 0.05% Tween 20, 100 mM β-mercaptoethylamine HCl, 10 mM Trolox, 20 mM L-cysteine, and 2 mM 2-mercaptoethanol.

FIG. 1 illustrates the primary sequencing metrics (error rate, percent phasing, and percent prephasing) presented with flowcell top surface (1) and bottom surface (2) at two different blue light power scales (1× and 1.2×) for both Read 1 and Read 2 during 2×151 cycles. It was observed that the new scan mix MTC provided higher green and blue remaining signal intensity (lower signal decay) and also lower % ER, phasing and prephasing values during the sequencing runs comparing to the standard scan mix VSM.

Example 2. Sequencing by Synthesis on NovaSeg™ Blue/Green Two-Channel System with High RI Scan Mixtures In this experiment, a new scan mix was tested on an Illumina NovaSeg™ instrument with standard PhiX 2×151 cycle sequencing run, with red and green laser imaging system. The incorporation mix contained the following ffNs: Green ffT (LN3-AF550POPOS0), Dark G, Red ffC (LN3-S07181), Red ffA (LN3-BL-AF670POPO), Green ffA (LN3-BL-NR550S0). Four different type of scan mix formulations were tested. The signal boost was calculated at the first cycle. The signal boost using the new scan mixtures was compared to the same sequencing run using a standard scan mix formulation comprising 1M Tris buffer, 20 mM sodium ascorbate, 10 mM HEG and 0.05% Tween 20.

Formulations of Type 1 contained glycine, sucrose, KCl, and Tris, in addition to the standard scan mix components (e.g., Formulation 1A included 160 mg/mL glycine, 80 mg/mL sucrose, 80 mg/mL KCl, and 50 mg/mL Tris. Formulation 1B was similar to formulation 1A except that sucrose was present at 50 mg/mL.

Formulations of Type 2 contained glycine, NaCl, Tris, and glycerol, in addition to the standard scan mix components. Formulation 2A included 160 mg/mL glycine, 50 mg/mL NaCl, 50 mg/mL Tris, and 4% glycerol by weight. Formulation 2B was similar to formulation 2A except that glycerol was present at 5% by weight. Formulation 2C was similar to formulation 2A except that glycine was present at 150 mg/mL, NaCl was present at 40 mg/mL, and glycerol was present at 5% by weight.

Formulations of Type 3 contained glycine, glucose, KCl, and Tris, in addition to the standard scan mix components. Formulation 3A included 150 mg/mL glycine, 50 mg/mL glucose, 80 mg/mL KCl, and 50 mg/mL Tris. Formulation 3B was similar to formulation 3A except that glucose was present at 80 mg/mL.

Formulations of Type 4 contained threonine, sucrose, KCl, and Tris, in addition to the standard scan mix components. Formulation 4A included 70 mg/mL threonine, 100 mg/mL sucrose, 80 mg/mL KCl, and 100 mg/mL Tris.

| Formulation | Lane | Read 1 Signal Boost | Read 2 Signal Boost |
|---|---|---|---|
| 1A | 1 | +32% | +52% |
| 1A | 2 | +35% | +56% |
| 1B | 1 | +23% | +27% |
| 1B | 2 | +21% | +25% |
| 2A | 1 | +25% | +44% |
| 2A | 2 | +20% | +37% |
| 2B | 1 | +13% | +30% |
| 2B | 2 | +26% | +45% |
| 2C | 1 | +30% | +39% |
| 2C | 2 | +25% | +34% |
| 3A | 1 | +20% | +27% |
| 3A | 2 | +28% | +33% |
| 3B | 1 | +26% | +35% |
| 3B | 2 | +24% | +32% |
| 4A | 1 | +32% | +34% |
| 4A | 2 | +32% | +34% |

In addition, the performance of freshly made scan mix formulations were also compared with that of the 14 days old formulations. No drop in performance was observed.

What is claimed is:

1. A method for reducing light-induced sequencing signal decay during sequencing by synthesis, comprising:

(i) contacting a solid support with an incorporation mixture comprising DNA polymerase and four different types of nucleotides A. C. G, and T or U, wherein the solid support comprises a plurality of different target polynucleotides immobilized thereon, and sequencing primers that are complementary and hybridized to at least a portion of the target polynucleotides;

(ii) incorporating one type of nucleotides into the sequencing primers to produce extended copy polynucleotides, wherein at least one of the four different types of nucleotides comprises a detectable label, and each of the four different types of nucleotides comprises a 3' blocking group;

(iii) imaging and performing one or more fluorescent measurements of the extended copy polynucleotides in an aqueous scan mixture to determine the identity of the incorporated nucleotides using one or more light sources operating at wavelengths between 450-460 nm and between 520-535 nm; and (iv) removing the 3' blocking groups and the detectable labels of the incorporated nucleotides;

wherein the aqueous scan mixture comprises one or more additives for reducing fluorescent signal decay caused by the fluorescent measurements, wherein the one or more additives comprise a salt or an ester of gallic acid, at least one triplet state quencher (TSQ), and one or more compounds selected from the group consisting of a radical scavenger, an oxygen scavenger, a reducing reagent, and combinations thereof, and wherein the method reduces signal decay by at least 10% after about 300 cycles when comparing to the method using an aqueous scan mixture without the at least one TSQ, and one or more compounds selected from the group consisting of an oxygen scavenger, a radical scavenger, a reducing reagent, and combinations thereof.

2. The method of claim 1, wherein the oxygen scavenger comprises an $O_2$ scavenger, and the radical scavenger comprises a reactive oxygen species (ROS) scavenger.

3. The method of claim 1, wherein the aqueous scan mixture further comprises at least one oxygen scavenger or at least one reducing reagent.

4. The method of claim 1, wherein the TSQ comprises a nickel (II) salt or complex, cyclooctatetraene (COT) or a substituted analog thereof, 2-mercaptoethylamine (MEA) or a salt thereof, 6-hydroxy-2,5,7,8-tetramethylchroman-2-carboxylic acid (Trolox) or a salt thereof, or combinations thereof.

5. The method of claim 1, wherein the oxygen scavenger comprises an enzyme capable of reacting with oxygen, glucose oxidase, catalase, diethylhydroxylamine (DEHA), hydroquinone, or combinations thereof.

6. The method of claim 1, wherein the radical scavenger comprises 1,4-diazabicyclo [2.2.2] octane (DABCO), caffeine, mannitol, or combinations thereof.

7. The method of claim 1, wherein the reducing reagent comprises a phosphine or a salt thereof, sodium sulfite ($Na_2SO_3$), a thiol containing compound, 2-mercaptoethanol (bME), cysteine or an analog thereof, or combinations thereof.

8. The method of claim 1, wherein the aqueous scan mixture comprises 2-hydroxylethyl gallate, a salt of MEA, Trolox, 2-mercaptoethanol, and cysteine or an analog thereof.

9. The method of claim 1, wherein the aqueous scan mixture has a basic pH of from about 7.2 to about 8.0.

10. The method of claim 1, wherein step (iii) comprises using two light sources operating at wavelengths between 450-460 nm and between 520-535 nm.

11. The method of claim 1, further comprising: step (v) contacting the solid support with an aqueous wash solution.

12. The method of claim 11, wherein steps (i) through (v) are repeated at least about 50 cycles to determine the target polynucleotides sequences.

13. The method of claim 12, wherein the method reduces sequencing error rate, percent phasing value, or percent prephasing value by at least 10% after about 300 cycles, when comparing to the method using an aqueous scan mixture without the one or more compounds selected from the group consisting of a TSQ, a radical scavenger, an oxygen scavenger, a reducing reagent, and combinations thereof.

14. A kit for use with a sequencing apparatus, comprising a scan mixture composition, the scan mixture composition comprising:

2-hydroxylethyl gallate, a salt of 2-mercaptoethylamine (MEA), Trolox, 2-mercaptoethanol, and cysteine or an analog thereof.

15. The kit of claim 14, further comprising an incorporation mixture composition for incorporating 3' blocked, labeled nucleotides into copy polynucleotide strands complementary to at least a portion of template polynucleotide strands, wherein the incorporation mixture composition comprises:

one or more different types of labeled nucleotides, wherein each of the labeled nucleotides comprises a 3' blocking group; and a DNA polymerase.

16. The kit of claim 14, wherein the concentrations of 2-hydroxylethyl gallate and Trolox in the scan mixture composition are independently from about 1 mM to about 50 mM, from about 5 mM to about 20 mM, or about 10 mM.

17. The kit of claim 14, wherein the concentration of the salt of MEA in the scan mixture composition is from about 10 mM to about 200 mM, or about 100 mM.

18. The kit of claim 14, wherein the concentration of 2-mercaptomethanol in the scan mixture composition is from about 1 mM to about 10 mM, or from about 2 mM to about 5 mM.

19. The kit of claim 14, wherein the concentration of cysteine or the analog thereof in the scan mixture composition is from about 1 mM to about 100 mM, from 5 mM to about 50 mM, or about 20 mM.

20. The method of claim 1, wherein the concentrations of the salt or ester of gallic acid in the scan mixture composition are independently from about 1 mM to about 50 mM, from about 5 mM to about 20 mM, or about 10 mM.

21. The method of claim 1, wherein the concentration of at least one TSQ in the scan mixture composition is from about 1 mM to about 100 mM.

22. The method of claim 1, wherein the concentration of the reducing reagent in the scan mixture composition is from about 1 mM to about 50 mM, or from about 2 mM to about 25 mM.

* * * * *